US011324896B2

(12) United States Patent
Knight et al.

(10) Patent No.: US 11,324,896 B2
(45) Date of Patent: May 10, 2022

(54) CAP FOR AN INJECTOR

(71) Applicant: UCB Biopharma SPRL, Brussels (BE)

(72) Inventors: Barry Alan Knight, Slough (GB); Marko Plevnik, London (GB); Norihiko Inoue, London (GB); Jamie Buckley, London (GB); Lisa Hornsey, London (GB)

(73) Assignee: UCB BIOPHARMA SPRL, Brussels (BE)

( * ) Notice: Subject to any disclaimer, the term of this patent is extended or adjusted under 35 U.S.C. 154(b) by 130 days.

(21) Appl. No.: 16/608,400

(22) PCT Filed: Apr. 25, 2018

(86) PCT No.: PCT/EP2018/060587
§ 371 (c)(1),
(2) Date: Oct. 25, 2019

(87) PCT Pub. No.: WO2018/197558
PCT Pub. Date: Nov. 1, 2018

(65) Prior Publication Data
US 2020/0306461 A1 Oct. 1, 2020

(30) Foreign Application Priority Data
Apr. 27, 2017 (GB) .................................. 1706697.8

(51) Int. Cl.
A61M 5/32 (2006.01)
(52) U.S. Cl.
CPC ........ A61M 5/3204 (2013.01); A61M 5/3257 (2013.01); A61M 5/326 (2013.01);
(Continued)

(58) Field of Classification Search
CPC .............. A61M 5/3204; A61M 5/3202; A61M 2205/0216
See application file for complete search history.

(56) References Cited

U.S. PATENT DOCUMENTS 4,378,015 A 3/1983 Wardlaw
4,553,962 A 11/1985 Brunet
(Continued)

FOREIGN PATENT DOCUMENTS

EP 2255842 A1 12/2010
EP 2878322 A1 6/2015
(Continued)

Primary Examiner — Bhisma Mehta
Assistant Examiner — Robert F Allen
(74) Attorney, Agent, or Firm — Muncy, Geissler, Olds & Lowe, P.C.

(57) ABSTRACT

Provided is a cap for an injector comprising a syringe with a needle cover. The cap comprises a cap body defining an inner and outer cap body; provided to the inner cap body, a grip for gripping the needle cover of said syringe; provided to the outer cap body, an opposing pair of recessed portions, wherein each recessed portion defines a recess base, and wherein each recessed portion is bounded by a peripheral lip; and provided to the recess base of each recessed portion, an over-coating. The cap body comprises a generally rigid material and each over-coating comprises a more flexible material. Each peripheral lip defines banks that extend beyond the over-coating of the recess base.

28 Claims, 23 Drawing Sheets

(52) U.S. Cl.
CPC ............... *A61M 2005/3263* (2013.01); *A61M 2005/3264* (2013.01); *A61M 2205/0216* (2013.01)

(56) References Cited

U.S. PATENT DOCUMENTS

| | | | | |
|---|---|---|---|---|
| 5,304,128 | A * | 4/1994 | Haber | A61M 5/2046 604/143 |
| 6,852,096 | B1 * | 2/2005 | Pouget | A61M 5/3257 604/110 |
| 6,872,190 | B1 | 3/2005 | Denis et al. | |
| 6,966,898 | B1 | 11/2005 | Pouget et al. | |
| 8,337,467 | B2 | 12/2012 | Rimlinger et al. | |
| 8,894,617 | B2 | 11/2014 | Painchaud et al. | |
| 8,945,053 | B2 * | 2/2015 | Vogt | A61M 5/3204 604/134 |
| 2009/0081103 | A1 | 3/2009 | Iannicelli et al. | |
| 2009/0090499 | A1 | 4/2009 | Lewis et al. | |
| 2010/0007395 | A1 | 1/2010 | Sugie | |
| 2012/0232491 | A1 * | 9/2012 | Jennings | A61M 5/3204 604/192 |
| 2012/0289905 | A1 * | 11/2012 | Julian | A61M 5/20 604/189 |
| 2013/0053788 | A1 | 2/2013 | Dugand et al. | |
| 2015/0182691 | A1 * | 7/2015 | McLoughlin | A61M 5/002 604/155 |
| 2016/0144132 | A1 * | 5/2016 | Scanlon | A61M 5/3204 604/192 |

FOREIGN PATENT DOCUMENTS

| | | |
|---|---|---|
| GB | 2438593 A | 5/2007 |
| WO | WO-99/22790 A1 | 5/1999 |
| WO | WO-00/09186 A2 | 2/2000 |
| WO | WO-2005/070481 A1 | 8/2005 |
| WO | WO-2007/083115 A1 | 7/2007 |
| WO | WO-2009/081130 A1 | 7/2009 |
| WO | WO-2009/081132 A1 | 7/2009 |
| WO | WO-2009/081133 A1 | 7/2009 |
| WO | WO-2010017650 A1 | 2/2010 |
| WO | WO-2010136078 A1 | 12/2010 |
| WO | WO-2013/006119 A1 | 1/2013 |
| WO | WO-2013/114017 A1 | 8/2013 |
| WO | WO-2014/146201 A1 | 9/2014 |
| WO | WO-2014/154498 A1 | 10/2014 |
| WO | WO-2015113172 A1 | 8/2015 |

* cited by examiner

CAP FOR AN INJECTOR

BACKGROUND

The present invention relates to a cap for an injector device for receipt of a syringe that is suitable for use in the injected delivery of a liquid drug formulation to a patient.

It is well-known to use syringes for the delivery of injectable liquid drug formulation to a patient. Syringes rely on puncturing of the patient's skin by a hollow needle through which the injectable liquid drug (e.g. in solution or suspension form) is delivered to the muscle or tissue of the patient. Typically, syringes comprise a barrel for containing a volume of the liquid drug; a hollow needle defining a needle tip for dispensing of the liquid; and a plunger that is axially movable within the barrel.

It is also well-known to provide injectors for use with syringes. Such injectors typically comprise a housing comprising one or more housing parts for housing the syringe and an actuating mechanism, which is actuable in use, to allow for delivery of the liquid drug formulation from the syringe. Both manual and automatic actuating mechanisms are known. Such actuating mechanisms are typically configured to provide drive for drivable movement of a drive transfer element (e.g. a plunger rod) that transfers drive to the plunger for axial movement thereof within the syringe barrel. Such movement of the plunger results in the plunged driving of the liquid drug from the syringe barrel to the hollow needle for dispensing to the patient via the needle tip thereof. Automatic actuating mechanisms typically comprise a source of drive power (e.g. a spring or a motor drive). Manual actuating mechanisms rely on the provision of manual drive by the user. The majority of injectors are configured as a device that incorporates both a syringe and an actuating mechanism in the same device housing.

For safety and hygiene reasons, it is desirable that the hollow needle is not exposed other than when expelling the liquid drug formulation during an injection procedure. Thus, syringes are typically provided with a needle cover defining a needle sheath arranged in a sheathing configuration for sheathing (e.g. sealing) of the forward portion of the needle and needle tip. In embodiments, the needle sheath is comprised of a (e.g. resiliently) compressible material such as a natural or synthetic rubber material. In embodiments, the needle cover is provided with a needle sheath cover for covering the needle sheath thereof.

In embodiments, the needle cover is arranged to connect/couple with a removable cap for a housing of the injector. Thus, when the removable cap is in a capped position the needle sheath and any needle sheath cover therefor is arranged for receipt of the needle tip of the syringe. When in the capped position, the needle tip is sheathed by the needle sheath, and when the cap is removed the needle sheath and any needle sheath cover therefor are also removed such as to thereby, unsheathe the needle tip.

In embodiments, the interior of the removable cap is provided with a grip (e.g. in the form of a connector defining one or more needle cover gripping elements) for gripping the needle cover (i.e. gripping the needle sheath and/or any needle sheath cover therefor). Such grip is arranged for gripping of the needle cover on removal of the cap such that removal of the cap also results in removal of the needle cover and hence, unsheathing of the needle tip.

It is desirable that injectors are arranged to allow for ease of removal of the cap from a housing thereof. In particular, it is desirable that such ready removal of the cap is enabled even when the device is made use of by patients whose manual dexterity is compromised (e.g. due to rheumatoid arthritis—an autoimmune disease characterized by chronic inflammation of the joints leading to progressive cartilage destruction and bone erosion). Such patients can potentially find the process of removing a cap from an injector to be a difficult challenge. In aspects, it is also desirable that such injectors are arranged to allow for ease of replacement of the removable cap to the housing, typically after an injection procedure have been completed.

Accordingly, there is provided a cap for use with an injector comprising a syringe with needle cover. The cap comprises a cap body defining an inner and outer cap body. The cap body may be provided as an assembly of two or more cap body parts. The inner cap body includes a grip for gripping a needle cover of a syringe. The outer cap body includes an opposing pair of recessed portions, wherein each said recessed portion defines a recess base, and wherein each recessed portion is bounded by a peripheral lip. The recess base of each recessed portion is provided with an over-coating. The cap body comprises a generally rigid material and each over-coating comprises a more flexible material. Each peripheral lip defines banks that extend beyond the over-coating of the recess base.

The opposing pair of recessed portions, each with over-coating, define a manual grip feature that is sized and shaped for manual gripping by the thumb and one or more finger of a user to allow for ready removal of the cap and needle cover from the injector. The use of such a manual grip feature has been found to be of practical utility even for those patients whose manual dexterity is compromised.

PCT publication no. WO2009/081103 A1 describes an injector for receipt of a syringe having a needle cover. The injector comprises a housing and a removable cap for the housing, wherein the removable cap is provided with a grip for gripping the needle cover arranged such that removal of the cap also results in removal of the needle cover and hence, unsheathing of the needle tip of the syringe.

PCT publication nos. WO2009/090499 A1 and WO2010/007395 A1 describe arrangements of a removable cap and a connector provided with needle cover gripping elements for gripping the needle cover arranged such that removal of the cap also results in removal of the needle cover and hence, unsheathing of the needle tip of the syringe.

SUMMARY OF THE INVENTION

According to one aspect of the present invention there is provided a cap for an injector comprising a syringe with a needle cover, said cap comprising a cap body defining an inner and outer cap body;

provided to said inner cap body, a metal connector defining plural needle cover gripping elements arranged around a central hub, wherein each gripping element is provided with one or more barbs for gripping the needle cover of said syringe;

provided to said outer cap body, an opposing pair of recessed portions, wherein each said recessed portion defines a recess base, and wherein each recessed portion is bounded by a peripheral lip; and provided to said recess base of each recessed portion, an over-coating, wherein said cap body comprises a generally rigid material and each said over-coating comprises a more flexible material, and wherein each said peripheral lip defines a bank that extends beyond the over-coating of the recess base.

These and other embodiments of the present invention are set forth in the later description, which describes for illustrative purposes only various embodiments thereof.

In relation to aspects of the injector with cap described herein the term 'forward' is used to mean that end of the injector, which locates closest to the injection site in use (i.e. the needle tip end) and the term 'rear' or 'rearward' is used to mean that end of the injector, which locates furthest from the injection site in use. The term axial herein is used by reference to an axis, which runs from the forward end of the cap and/or injector to the rearward end thereof, and which typically corresponds to the axis of the syringe.

There is provided cap for an injector. The injector comprises a syringe with needle cover.

In embodiments, the injector comprises a housing for at least partially housing said syringe and said cap is arranged for mating receipt by said housing of the injector.

In embodiments, the cap body defines a generally rectangular cuboid profile having four generally rectangular cap body sides. In other embodiments, the cap body defines a generally cylindrical profile or tapering cylindrical profile.

In embodiments, each recess base with over-coating defines a profile that corresponds with a rectangular cap body side but is recessed relative thereto.

In embodiments, the banks of each peripheral lip rise up in angular fashion from the over-coating of the recess base. In embodiments, at least forward and rear bank portions of the peripheral lip rise up at an angle of from 30° to 60° to the surface of the over-coating of the recess base.

In embodiments, the over-coating is provided as an over-moulding to the recess base.

There is provided a cap for use with an injector device that is arranged for use with a syringe that typically contains a liquid drug formulation. The syringe is suitable for use in the injected delivery of the liquid drug formulation to a patient. In embodiments, the injector comprises a housing (e.g. comprised of one or more housing parts) for housing the syringe.

In embodiments, the injector comprises a manual or automatic actuating mechanism, which allows for delivery of the liquid drug formulation from the syringe.

The cap body defines an inner cap body and an outer cap body. In embodiments, the cap body defines a generally rectangular cuboid profile having four generally rectangular cap body sides. In embodiments, the cap body cuboid profile defines a generally square rear opening. In embodiments, the housing defines a generally square cap-receiving forward profile arranged for mating receipt by the rear opening of the cap body. In embodiments, the housing defines a collar arranged for mating receipt by the rear opening of the cap body. In embodiments, one or more of the edges of the generally rectangular cuboid profile are rounded, much like the rounded edges of a dice. In embodiments, one or more of the edges of the generally square cap-receiving profile are similarly rounded.

In embodiments, the cap body comprises a generally rigid material. In embodiments, the cap body defines a hard material. In embodiments, the cap body comprises a plastic polymer material such as a thermoplastic polymer material such as a thermoplastic polypropylene material. In embodiments, the cap body comprises a polycarbonate/acrylonitrile butadiene styrene (ABS) blend. In other embodiments, the cap body comprises a polycarbonate material. In embodiments, the housing is of moulded form. In embodiments, the housing is comprised of a material that is of resilient character.

The inner cap body is provided with a grip for gripping a needle cover of a syringe. In embodiments, the grip is integrally formed with the inner cap body. In other embodiments, the grip is provided to the inner cap body as a separate insert part.

In embodiments, the cap body comprises a first cap body part in the form of a sleeve having forward and rear openings; a second cap body part in the form of a plug arranged for receipt by the forward opening of said sleeve form first cap body part, wherein the plug form second body part defines a plug top and an inner plug body; and provided to the inner plug body, the grip for gripping the needle cover of the syringe. On assembly of the first and second cap body parts, the plug top forms a cover for the forward opening of the sleeve form first cap body part, and the grip for gripping the needle cover of the syringe extends into the sleeve form first cap body part. In normal use, the syringe with needle cover is thus, inserted into the rear opening of the sleeve form first cap body part.

In embodiments, the cap body is provided with a connector defining one or more needle cover gripping elements for gripping the needle cover (i.e. gripping the needle sheath and/or any needle sheath cover therefor). In embodiments, such gripping elements are arranged for gripping of the needle cover when in the capping position. In embodiments such gripping elements are (e.g. additionally) arranged for gripping of the needle cover on removal of the cap such that removal of the cap also results in removal of the needle cover and hence, unsheathing of the needle tip. In embodiments, the needle cover gripping elements are arranged to project away from the top inner surface of the inner cap body and towards its open end.

In embodiments, the connector comprises one or more needle cover gripping elements (e.g. gripping legs) attaching to a central hub. In embodiments, the connector is in the form of a cage-like needle cover gripper. In embodiments, each gripping element (e.g. leg) is provided (e.g. at the foot thereof) with one or more gripping protrusions such as one or more internally facing hooks or barbs. In embodiments, the internally facing hooks or barbs are disposed at an angle with respect to the gripping leg. In embodiments, the connector locates within the cap such that the central hub locates adjacent to or slightly spaced from the top inner cap wall or surface and the gripping legs project away from the top inner cap wall or surface and towards the open end of the cap. Needle cover gripper arrangements are disclosed in PCT publication no. WO2009/081103 A1, the entire contents of which are incorporated herein by reference.

In embodiments, the cap is provided with a connector. In embodiments, the connector is formed of metal such as stainless steel. In embodiments, a boss is defined at the inner end wall of the inner cap body and the connector is arranged for receipt within said boss. The connector is shaped to fit within and engage the needle cover and in embodiments, also to engage the inner part of the removable cap. In embodiments, the connector includes one or more needle gripper elements in the form of first legs attaching to a central hub and spaced symmetrically away from one another, each first leg having one or more internally facing barbs pointing toward a forward region of the connector and adapted to engage a proximal region of the needle cover. In embodiments, the one or more internally facing barbs are disposed at an angle with respect to the first leg. In embodiments, the connector also includes one or more second legs spaced symmetrically away from one another, each second leg having one or more externally facing barbs located in the forward region of the connector and adapted to engage a forward region of the inner part of the removable cap or cap insert. In embodiments, the one or more first legs are biased initially at about 60 to 80 degrees with respect to the horizontal. In embodiment, the second legs are shorter than the first legs. Arrangements of removable cap and connector of this type are disclosed in PCT publication nos. WO2009/090499 A1 and WO2010/007395 A1, the entire contents of which are incorporated herein by reference.

In embodiments, particularly wherein the connector comprises one or more needle cover gripping elements (e.g. gripping legs) attaching to a central hub, it is desirable to position the connector within the removable cap such that the central hub is in spaced relationship to the top inner cap wall of the removable cap. When so-positioned, the gripping legs project away from the top inner cap wall and towards the open end of the cap.

In embodiments, the cap body, particularly the second cap body part, has a protruding pocket for receiving a connector, and the connector comprises a base; a plurality of first legs spaced symmetrically away from one another and extending proximally from the base; and a plurality of second legs extending proximally from the base and having a tip that flares outwardly towards the protruding pocket, wherein at least one of the second legs is positioned between two of the first legs. In embodiments, a first leg includes internally facing barbs that engage a needle sheath cover that covers the needle of the syringe assembly. In embodiments, the internally facing barbs include a tip that flares inward and towards the base. In embodiments, the tip of at least one of the first legs dig into the needle cover. In embodiments, the tip of at least one of the second legs engages the protruding pocket. In embodiments, the internally facing barbs are concaved.

In embodiments, the internally facing barbs extend at an angle with respect to the principal axis of the connector/cap. In embodiments, at least one of the first legs includes an upright and a first pair of internally facing barb tips positioned to a lateral side of the upright and a second pair of internally facing barb tips positioned to a medial side of the upright. Arrangements of removable cap and connector of this type are disclosed in PCT publication no. WO2010/007395 A1, the entire contents of which is incorporated herein by reference.

The outer cap body is provided with an opposing pair (i.e. first and second) of recessed portions. Thus, in embodiments, where the outer cap body is of rectangular cuboid form, a first recessed portion locates on a first generally rectangular cap body side and a second recessed portion locates on an opposing second generally rectangular cap body side.

Each recessed portion defines a recess base. In embodiments, the recess base defines a generally flat profile.

An over-coating is provided to the recess base of each recessed portion. The over-coating comprises a material that is more flexible (e.g. softer) than the generally rigid material of the cap body. In normal use, the over-coating acts to provide a grip surface for the user's index finger or thumb. In embodiments, the over-coating allows for creation of a bond (e.g. chemical) with at least the recess base of each recessed portion of the cap body, enabling both parts to work as a hybrid grip surface providing finger-gripping properties.

In embodiments, the over-coating is provided as an over-moulding to the recess base. In embodiments, the cap body is formed by a first moulding process and the over-coating is provided by a second moulding process. In embodiments, the cap body and over-coating have a co-moulded form.

In embodiments, the over-coating comprises a thermoplastic elastomer material. In embodiments, the over-coating is comprised of a thermoplastic elastomer (TPE) material selected from the group consisting of styrene-ethylene/butylene-styrene (SEBS) block copolymers (such as those sold under the trade name Kraton) where the ethylene/butylene mid-block is a random copolymer which confers rubber like properties. The hardness and resilience of the TPE can be determined by the relative proportion of the styrene and ethylene/butylene blocks and the addition of compounding agents such as mineral fillers and extender oils. Such TPE formulations are sold under the trade names Kraiburg, Mediprene and Versaflex. In embodiments the TPE material may alternatively be based on polymers from the groups Styrene-Ethylene/Propylene-Styrene (SEPS) block copolymers (e.g. Kraton, Septon), Styrene-Butadiene-Styrene (SBS), thermoplastic vulcanisates (TPV) incorporating vulcanised rubber inclusions (e.g. Santoprene). Similar considerations to the optimisation of properties apply as in the case of SEBS. In embodiments blends of the aforementioned polymers may also be utilised. In embodiments, the thermoplastic elastomer material is that sold under the trade name Meliflex M8605 by Melitex A/S of Hartvig Jensensvej 1, DK-4840, Nr. Alslev, Denmark.

Each recessed portion is bounded by a peripheral lip, wherein each peripheral lip defines a bank that extends beyond the over-coating of the recess base. That is to say, the bank stands proud of the over-coating of the recess base. In embodiments, the peripheral lip of each recessed portion defines a generally rectangular profile, and thus four bank portions are defined (e.g. forward, rear and first and second side bank portions). In embodiments, the generally rectangular profile has rounded corners and thus, the peripheral lip is continuous, but with four distinct bank and rounded corner portions.

In embodiments, the banks of each peripheral lip rise up in angular fashion from the over-coating of the recess base. In embodiments, at least the forward and rear banks of the peripheral lip rise up at an angle of from 30° to 60°, preferably between 40° and 50° (e.g.) 45°, to the surface of the over-coating of the recess base.

In embodiments, the banks of the peripheral lip ramp has a rounded top (i.e. summit) profile.

In normal use, the bank, particularly the forward and rear portions thereof, acts to provide a reaction surface for the user's index finger or thumb. Dependent on whether the cap is being removed or replaced, that reaction surface may receive pulling or pushing force applied by the user.

In embodiments, each recess base with over-coating defines a profile that corresponds with a rectangular cap body side but is recessed relative thereto.

There is also provided an injector herein comprising a housing; a syringe with a needle cover; and a cap as described herein. In embodiments, the housing comprises one or more housing parts for housing the syringe. In embodiments, the cap fits over and thereby, acts such as to close off, the forward end of the housing. In embodiments, when in the capped position, the removable cap acts such as to prevent ingress of contaminants into the housing of the injector.

In embodiments, the cap body defines a generally rectangular cuboid profile having four generally rectangular cap body sides and having a generally square rear opening. In embodiments, the housing defines a generally square cap-receiving forward profile.

In embodiments, a rear opening of the cap body is provided with mating protrusions arranged for mating receipt of a collar provided to the forward end of housing.

In embodiments, the housing defines a housing cavity. The housing cavity is arranged for receipt of a syringe and is therefore typically sized and shaped for this purpose. The housing may be arranged as a single part or a multi-part (e.g. two part) housing assembly.

In embodiments, the syringe is movable within the housing such as in a direction parallel with or along the drive axis. In embodiments, the syringe is movable within the housing from a first position, in which the needle tip of the syringe is within the housing to a second position, in which at least the needle tip protrudes from a needle projection aperture thereof.

The injector comprises a syringe. The syringe is typically arranged for receipt within the housing cavity. In embodiments, the syringe comprises a syringe barrel for holding a volume of a liquid drug formulation; a hollow needle at a front end of the barrel, the hollow needle defining a needle tip for dispensing of the liquid drug formulation; and a plunger (e.g. in the form of a rubber stopper) that is axially movable within the syringe barrel. The syringe plunger is movable axially within the barrel so as to enable the liquid drug formulation to be expelled from the barrel and thence through the hollow needle via the dispensing tip for injection into the patient. The syringe barrel is typically comprised of glass but may also be comprised of a relatively hard plastic polymer such as hardened polyethylene, polycarbonate or cyclic olefin polymers.

In embodiments, the plunger is comprised of a natural or synthetic polymer friction material, which frictionally interacts with the side wall of the syringe barrel. Suitable plunger materials include natural or synthetic rubbers or elastomeric materials.

In more detail, the syringe barrel is selected such as to define a barrel chamber for containing a suitable volume of the liquid drug formulation. In embodiments, that suitable volume is selected to correspond to a single dose of the drug formulation to be delivered to the patient. In other words, delivery of that single dose involves expelling the majority of the liquid drug formulation contents of the barrel chamber through the hollow needle for injection into the patient.

In embodiments, the rear end of the syringe barrel is provided with an end flange. In embodiments, the forward end of the syringe barrel is shaped to provide a shoulder. In embodiments, forward of that shoulder the syringe narrows further into a neck, which typically forms the needle-holding part thereof.

The syringe further comprises a needle cover, which in embodiments, defines a needle sheath arranged in a sheathing configuration for sheathing (e.g. sealing) of the needle tip.

In embodiments, the needle sheath is comprised of a (e.g. resiliently) compressible material such as a natural or synthetic rubber material. In a storage configuration, the needle tip sticks into (e.g. is spiked or staked into) the needle sheath such that sealing of the needle tip is achieved. Usually, at least the first 3 to 4 mm of the needle tip end is so sheathed. It will be appreciated that for clinical reasons, the sealing of the needle tip acts in embodiments, such as to prevent passage of contaminant, bacterial or otherwise, through the needle tip and thus into the needle bore and syringe barrel chamber. Sterile sealing is preferred.

In embodiments, the needle cover is provided with a needle sheath cover for covering the needle sheath thereof. In embodiments, the needle sheath cover is comprised of a rigid material (e.g. polypropylene) and may sometimes be referred to as a rigid needle shield. In embodiments, the needle sheath cover is provided with one or more gripping elements (e.g. hooks) arranged for gripping of the needle sheath. In embodiments, the needle sheath is provided with one or more features arranged for receipt of the one or more gripping elements such as one or more indents, grooves or cavities.

In embodiments, the needle cover projects within the cap such that when the removable cap is in the capped position the needle sheath and any needle sheath cover therefor is arranged for receipt of the needle tip of the syringe. In such embodiments, when in the capped position, the needle tip is sheathed by the needle sheath, and when the cap is removed the needle sheath and any needle sheath cover therefor are also removed such as to thereby, unsheathe the needle tip. In embodiments, the cap defines an essentially closed cap chamber, optionally tapering, and the needle sheath and any needle sheath cover are provided along the axis of that chamber.

In embodiments, the syringe barrel is provided with a syringe carrier that is arranged to fit over part or all of the length of the needle barrel. The syringe carrier may also extend out beyond the syringe barrel to wholly or partly enclose a length of the forward shoulder of the syringe barrel and of the hollow needle that extends from (the forward shoulder) of the syringe barrel.

In embodiments, the syringe carrier is arranged for receipt by the syringe barrel and fits at least partly over the flange of the rear end of the syringe barrel. In embodiments, the syringe carrier is arranged for snap fitting over the end flange of the syringe. In embodiments, the flange is effectively capped by the relevant 'end flange' part of the syringe carrier. In embodiments, a syringe flange guard element is provided to the syringe carrier.

In embodiments, one or more positioning and/or retaining features are provided to the housing for positioning and/or retaining the syringe and/or syringe carrier in the housing cavity. In embodiments, the one or more positioning and/or retaining features comprise one or more snap features provided interiorly to the housing.

The hollow needle of the syringe defines a needle bore, which is most typically of circular cross-section and of selected bore diameter. It may be appreciated that in embodiments, the bore diameter may affect the force required to expel the liquid drug formulation through the needle and also the velocity at which the liquid drug formulation is expelled.

Examples of typical needles that are suitable for use therein include 12.5 mm ("half inch") long thin wall needles of grade 23G, 25G or 27G. These have a needle bore of from about 0.2 to 0.4 mm such as from 0.24 to 0.37 mm. Other examples include both regular and thin wall needles used in conventional syringes including those with bevels such as 3 and 5 bevels.

Typically, the housing and/or any inner housing sub assembly thereof is provided with a barrel receiving part for receiving the barrel of the syringe; a plunger receiving part for receiving the plunger of the syringe; and in embodiments, a needle receiving part for receiving the hollow needle of the syringe.

In embodiments, the plunger receiving part of the housing and/or any inner housing sub assembly thereof allows the plunger within the syringe barrel to be received thereby and for the plunger to be movable (e.g. axially) therein from a first position to a second position, in which it is moved somewhat into the syringe barrel. During use the plunger is in embodiments, movable to a fully plunged position at which, in most embodiments all of the liquid drug formulation contents of the barrel have been expelled.

In embodiments, the needle receiving part of the housing and/or any inner housing sub assembly thereof includes a needle projection aperture through which the hollow needle may protrude from the housing, for example during expelling of the liquid drug formulation through the hollow needle and its needle tip for delivery to the patient.

In embodiment, the syringe is fixed within the housing. In embodiments, a protective shroud (e.g. spring-mounted) is provided to protect the needle of the syringe. In embodiments, the protective shroud is movable (e.g. against the biasing force of a spring) to expose the needle. In embodiments, when the needle is retracted from the skin of the patient, the protective shroud returns under the biasing force of the syringe, and in embodiments, locks out, thereby preventing the device from being reused.

In embodiments, the syringe is movable within the housing cavity from a rest position, in which the needle tip is within the housing to a use position, in which the needle tip protrudes from the needle projection aperture.

Where the syringe is movable in the housing, it may desirable for safety and hygiene reasons that the needle does not protrude from (i.e. out with) the housing other than when expelling the liquid drug formulation during an injection procedure. Thus, the housing and/or any inner housing sub assembly thereof and housing cavity defined thereby may be arranged such that the needle receiving part thereof allows for the needle of the syringe to be axially moveable therein from a first position in which the needle is wholly housed (or shrouded) by the needle receiving part to a second position in which at least the tip of the needle protrudes from that needle receiving part of the housing.

In embodiments, where the syringe is movable within the housing, the housing may include biasing means (e.g. a return spring) arranged such that the needle is normally biased towards the first position, wherein such biasing means are overcome during the actuation of the syringe (e.g. by an actuating mechanism) to allow for movement of the needle to the second position.

In embodiments, the injector further comprises an actuating mechanism. In use, the actuating mechanism is actuable to allow for delivery of the liquid drug formulation from the syringe. Both manual and automatic actuating mechanisms are suitable. In embodiments, the actuating mechanism is configured to provide drive for drivable movement of a drive transfer element (e.g. a plunger rod) that transfers drive to a plunger of the syringe for axial movement thereof within the syringe barrel. Such movement of the plunger results in the plunged driving of the liquid drug from the syringe barrel to the hollow needle for dispensing to the patient via the needle tip thereof. Automatic actuating mechanisms typically comprise a source of drive power (e.g. a strong spring or a motor drive). Manual actuating mechanisms rely on the provision of manual drive by the user.

In terms of function, the injector is arranged to allow for actuation (i.e. firing) of the syringe. In embodiments, the injector thus, also includes a drive transfer element for transferring axial drive to the plunger of the syringe. In embodiments, the plunger end part of the drive transfer element is partly or wholly comprised of a natural or synthetic polymer friction material, which frictionally interacts with the side wall of the syringe barrel. Suitable plunger end materials include natural or synthetic polymers or elastomeric materials.

In embodiments, the injector is a manual injector. In embodiments, the manual injector comprises a manually operable drive transfer element for transferring axial drive to the plunger of the syringe. In embodiments, the manual injector comprises one or more finger hold elements, for example in the form of a handle, to allow the user to hold the injector with the fingers of a hand, and typically to provide drive force to the drive transfer element by way of a thumb pushing action.

In embodiments, the manual injector comprises a handle having a first flange and a second flange forming a handgrip; a first arc forming a bottom surface of the first flange contoured to correspond to a radius of an arc formed by a user's fingers; and a second arc forming a bottom surface of the second flange contoured to correspond to a radius of an arc formed by the user's fingers. In embodiments, the first and second arcs are of corresponding form and symmetrically arranged. In other embodiments, the second arc is shaped flatter than the first arc. Manual injectors of this general type are described in PCT publication no. WO2009/090499 A1, the entire contents of which is incorporated herein by reference.

In embodiments, the manual injector includes a safety mechanism for covering off and/or retracting the syringe after use. In embodiments, the manual injector includes a syringe support; a protective housing sheath for protecting an injection needle carried by the syringe, the housing sheath being mounted to slide relative to the syringe support between an injection position in which the needle is uncovered, and a protection position in which the needle is covered, the housing sheath having a grip surface enabling the device to be gripped by a user; and a return spring for urging the housing sheath into the protection position, wherein the sheath also includes an extender member for extending the grip surface, fitted on the housing sheath in such a manner as to present a larger grip surface. Manual injectors of this type are described in US publication no. US2013/0053788 A1, the entire contents of which is incorporated herein by reference.

In embodiments, the manual injector comprises a housing; a syringe comprising a syringe barrel and a plunger; a manually operable drive transfer element for transferring drive to said plunger of the syringe for axial movement thereof within said syringe barrel; a handle having a handle body; and an opposing pair of handle arms; and a cap as described herein. The cap is arranged for receipt by the housing such that the opposing pair of recessed portions on the outer cap body line up with the opposing pair of handle arms. In such lined up orientation, it will be appreciated that the axis defined by the opposing arms lies in a plane perpendicular to the plane defined by each of the recess bases.

In embodiments, the housing defines a generally rectangular cuboid profile having four generally rectangular cap body sides and having a generally square rear opening, and the housing defines a generally square cap-receiving forward profile. It will be appreciated that in such embodiments, only four possible orientations of cap receipt by the housing are possible, corresponding to 0°, 90°, 180° and 270° and that typically, in only two of the possible orientations (e.g. 0° and 180° or alternatively 90° and 270°) will the opposing pair of recessed portions on the outer cap body line up with the opposing pair of handle arms.

Representative manual injectors that may be modified in accord with the present invention include those described in U.S. Pat. Nos. 6,852,096; 6,872,190; 6,966,898; 8,337,467; and 8,894,617, all of which are incorporated herein by reference.

In embodiments the injector is an auto-injector. In embodiments, the auto-injector includes an energy store for storing energy that can then be released to provide the axial drive to the syringe via the drive transfer element. In embodiments, the energy store comprises a mechanical energy store such as a spring (e.g. a compression or torsion spring). In other aspects, the energy store may be provided by a container of compressed liquid or gas propellant that on release provides a source of jet energy propulsion.

In embodiments, the energy store is able to exert an axial drive force of up to 60 N on the syringe. Where the energy store is a compression spring the force exerted typically varies over the actuation profile such as from a range of 60 to 40 N at the start of actuation to from 40 to 20 N at the end of the actuation profile. Where the energy store is a compressed liquid or gas propellant a more constant force is typically exerted over the actuation profile.

In embodiments, release of axial drive force (e.g. actuation of the actuating mechanism) is responsive to a trigger (e.g. a user-actuable trigger). In embodiments, the trigger comprises a button, switch or lever arrangement. In other embodiments, a press actuation mechanism that is actuable in response to pressing of the housing of the device against the skin is envisaged.

In embodiments, the auto-injector includes a first coupling for coupling the drive transfer element to the syringe barrel of the syringe. In embodiments, the drive transfer element is a plunger rod.

In embodiments, the first coupling is a reversible (e.g. demountable) coupling arranged for decoupling (e.g. demounting) when the syringe moves to the use position. In embodiments, the first coupling is at a forward position of the drive transfer element. Thus during a use operation, the first coupling is initially in place and axial drive force applied to the drive transfer element (e.g. drive shuttle) results in drivable movement of the syringe from the rest to the use position. That first coupling then decouples such that further axial drive force applied to the drive transfer element (e.g. drive shuttle) results in drivable movement of the syringe plunger within the syringe barrel, ultimately to a fully plunged position when most, preferably all of the liquid drug formulation contents of the syringe barrel have been drivably expelled therefrom.

In embodiments, the drive shuttle has an axially symmetric form such as cylindrical form, wherein the plunger rod for the syringe plunger (e.g. rubber stopper form) is suitably received axially within the cylindrical form. Guides (e.g. a central aperture of an end wall) may be provided to the shuttle to assist that axial receipt.

Thus, in embodiments, the energy store communicates with the drive transfer element via a second coupling, wherein the second coupling is a reversible coupling arranged for decoupling when the plunger end of the drive transfer element moves to a position that results in full plunging of the syringe plunger within the syringe barrel (e.g. provided by reversible coupling of the drive shuttle to the plunger rod and sleeve as described above). Thus, the second coupling is a reversible (e.g. demountable) coupling arranged for decoupling (e.g. demounting) when the syringe plunger has been moved to a fully plunged position. Ideally in use, once decoupled from the energy store (i.e. source of axial drive force) the drive transfer element is free to move such that reverse axial movement thereof is unhindered. A needle retract mechanism may then be arranged (e.g. responsive to a needle return spring) to retract the syringe needle back into the housing unhindered by any interaction with the now free to move drive transfer element. Or alternatively, a needle shroud mechanism may be arranged to be activated at this point.

In embodiments, the auto-injector additionally comprises a second coupling for coupling the drive transfer element to a source of axial drive, wherein said second coupling is a reversible coupling arranged for decoupling when the syringe plunger moves to a fully plunged position within the syringe barrel.

In embodiments, a reset mechanism is provided for resetting the firing mechanism after actuation thereof. The reset mechanism may for example, comprise a spring, motor, mechanical arrangement or a reset coupling.

Representative auto-injectors that may be modified in accord with the present invention include those described in U.S. Pat. Nos. 4,553,962; 4,378,015; 5,304,128 and PCT patent publication nos. WO99/22790 A1 (Elan Corporation); WO00/09186 A1 (Mediject Corporation); WO2010/017,650 A1; WO2010/136,078 A1; WO2014/146,201 and WO2015/113,172 (TecPharma Licensing AG); WO2005/070,481 A1 and WO2007/083,115 A1 (The Medical House PLC) and PCT patent publications nos. WO2009/081,103, WO2009/081,130, WO2009/081,132, WO2009/081,133 and WO2010/007,395 (UCB Pharma SA), all of which are incorporated herein by reference.

There is also provided cap for an injector comprising a syringe with a needle cover, said cap comprising
  a first cap body part in the form of a sleeve having forward and rear openings;
  a second cap body part in the form of a plug arranged for receipt by said forward opening of said sleeve form first cap body part, wherein said plug form second body part defines a plug top and an inner plug body, and wherein said inner plug body defines a protruding pocket; and
  arranged for receipt within said protruding pocket of the inner plug body, a metal connector defining plural needle cover gripping elements arranged around a central hub, wherein each gripping element is provided with one or more barbs for gripping the needle cover,
  wherein the first cap body part, second cap body part and connector are provided as separate parts, and wherein in the assembled cap, the plug top of the plug form second cap body part forms a cover for the forward opening of the sleeve form first cap body part, and the needle cover gripping elements of the connector extend into the sleeve form first cap body part.

In embodiments, the outer of the sleeve form first cap body part is provided with opposing pair of recessed portions, wherein each said recessed portion defines a recess base, and wherein each recessed portion is bounded by a peripheral lip; and
  provided to said recess base of each recessed portion, an over-coating,
  wherein said cap body comprises a generally rigid material and each said over-coating comprises a more flexible material,
and wherein each said peripheral lip defines a bank that extends beyond the over-coating of the recess base.

According to a further aspect of the present invention there is provided a kit of parts comprising an injector as described above but absent the syringe; and a syringe containing a liquid drug formulation.

According to a further aspect of the present invention there is provided a kit of parts comprising an injector as described above but absent the syringe; and packaging therefor; and optionally a syringe containing a liquid drug formulation.

Suitable packaging typically comprises a container for the injector and syringe. In embodiments, the packaging comprises a compartment for the auto-injector pre-loaded with the syringe. In embodiments, the packaging comprises a separate compartment for a 'kit' of the injector and the syringe.

BRIEF DESCRIPTION OF THE DRAWINGS

The disclosure is further described with reference to the accompanying drawings, in which:

FIGS. 6A and 6B are side-on views of the injector of FIGS. 1A and 1B in use by a user, wherein FIG. 6A shows a first cap removal process and FIG. 6B shows a second cap removal process;

FIGS. 12A and 12B are side-on views of the injector of FIGS. 9 to 11 in use by a user, wherein FIG. 12A shows a first stage of a first cap removal process and FIG. 12B shows a second stage of a first cap removal process; and FIGS. 13A and 13B are side-on views of the injector of FIGS. 9 to 11 in use by a user, wherein FIG. 13A shows a first stage of a second cap removal process and FIG. 13B shows a second stage of a second cap removal process.

DETAILED DESCRIPTION

To provide an overall understanding of the systems, devices and methods described herein, certain illustrative embodiments will now be described. For the purpose of clarity and illustration these systems and methods will be described with respect to injectors that are arranged to receive a syringe. It will be understood by one of ordinary skill in the art that the systems, devices and methods described herein may be adapted and modified as is appropriate, and that these systems, devices and methods may be employed in other suitable applications, and that other such additions and modifications will not depart from the scope hereof.

Figure 1A:
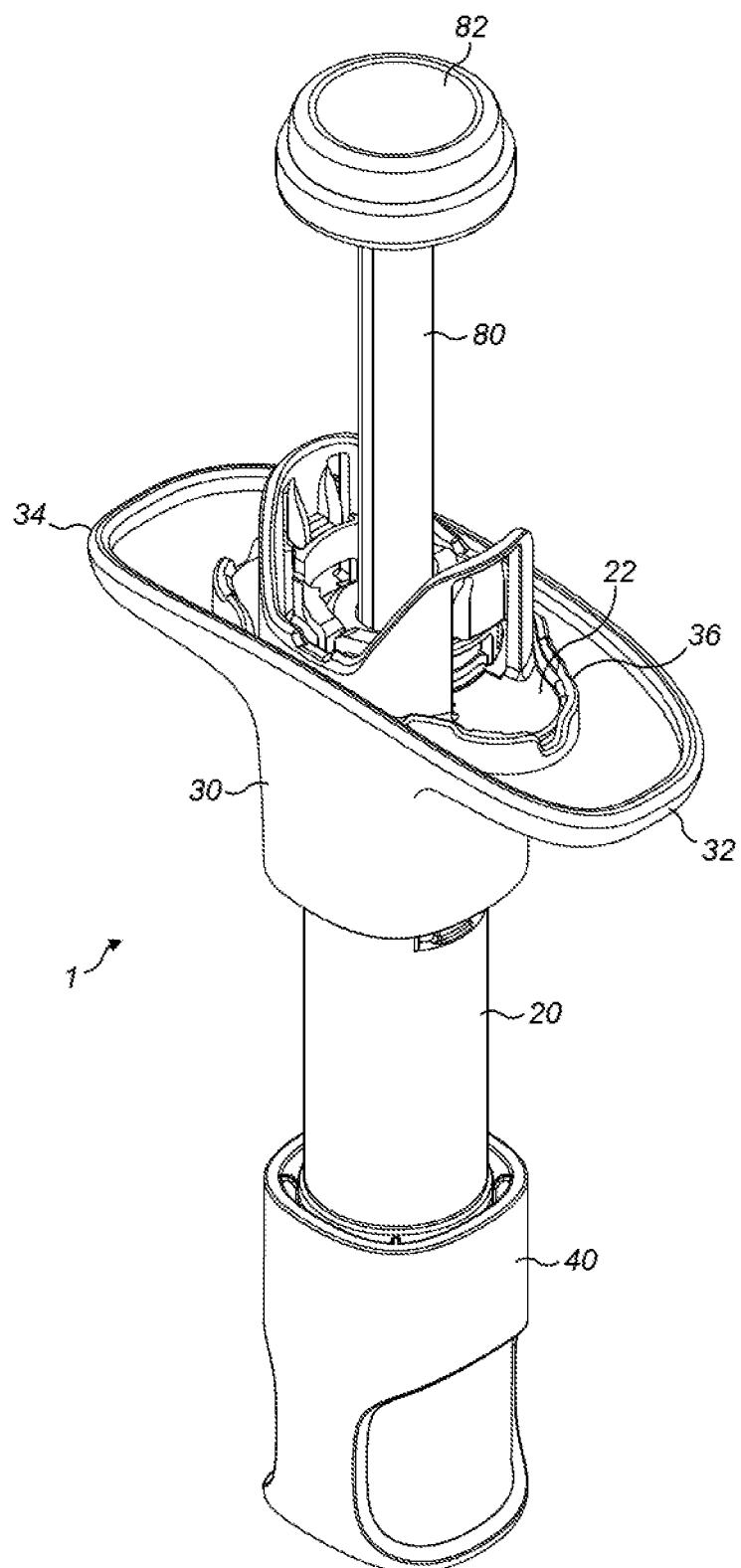
FIGS. 1A and 1B are respectively perspective and side views of an injector herein in the 'pre-use' position with a removable cap thereof in docked receipt by a housing thereof.
Figure 1B:
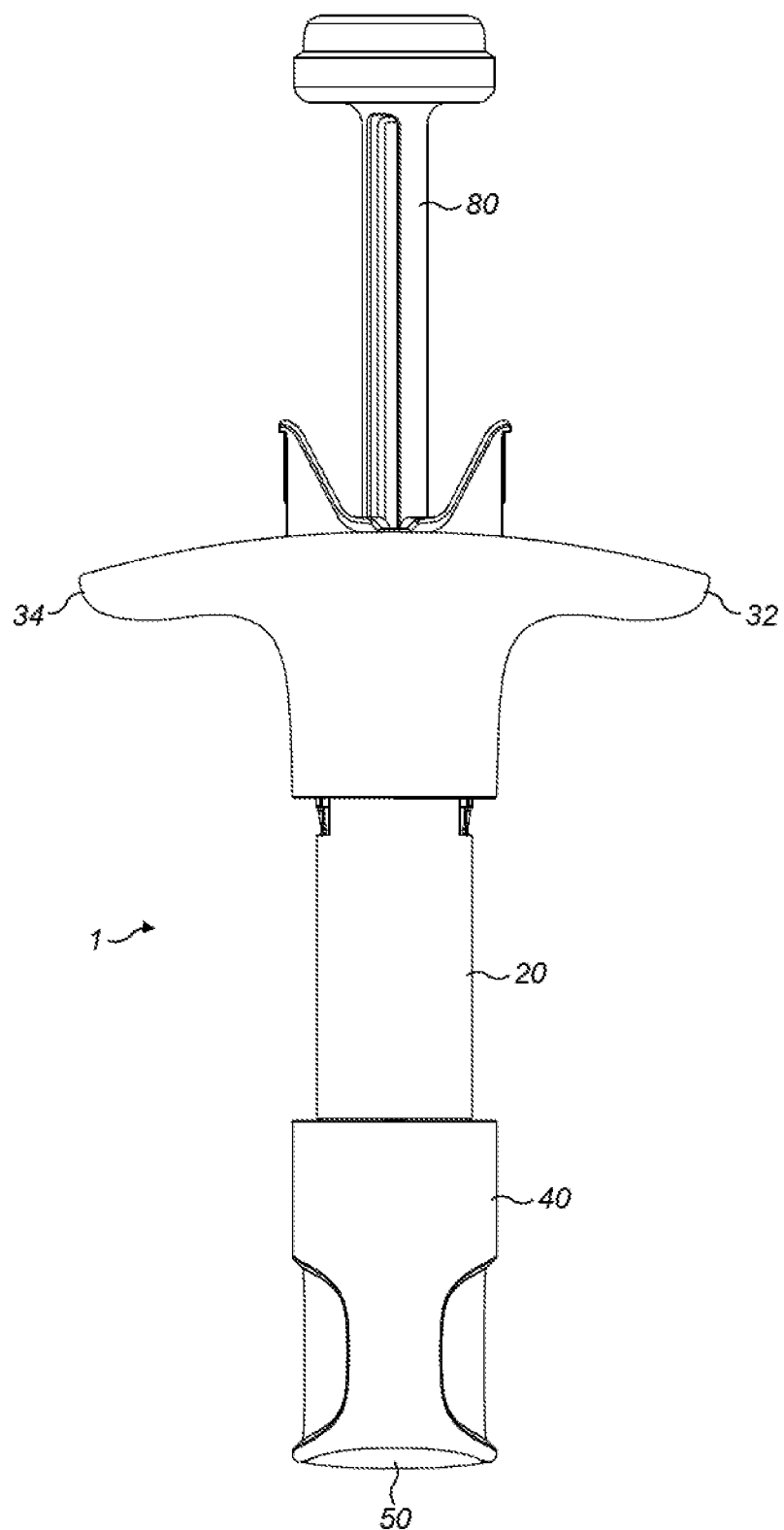
Figure 2:
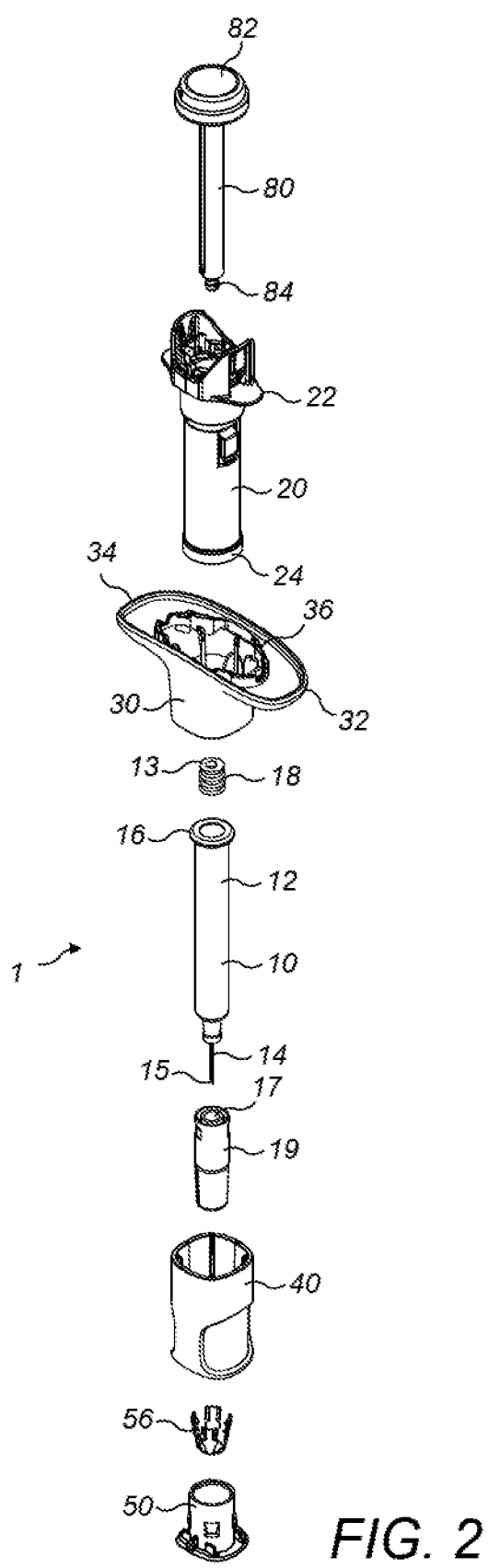
FIG. 2 is an exploded view of the injector of FIGS. 1A and 1B.

Referring now to the drawings, FIGS. 1A, 1B and 2 show aspects of a manual injector 1 herein, which is arranged for use with a syringe 10 that contains a liquid drug formulation. FIGS. 1A and 1B shows the injector 1 in a capped (pre-use) configuration and FIG. 2 shows an exploded view of the injector. The injector 1 comprises a generally cylindrical form housing 20, which is arranged for receipt of the syringe 10 and is sized and shaped for this purpose.

As may be seen at FIG. 2, the syringe 10 comprises a barrel 12 for holding the liquid drug formulation; a hollow needle 14 with needle tip 15 at a forward end of the barrel 12; a syringe flange 16 at the rear end of the barrel; and a syringe plunger 18 in the form of a rubber stopper that is arranged for axial movement within the barrel 12 in response to driven movement of a drive transfer element in the form of manually operable plunger rod 80 such as to enable the liquid drug formulation to be expelled through the hollow needle 14. The hollow needle 14 defines a needle bore, which is of circular cross-section (e.g. 23G, 25G or 27G bore diameter) and a needle tip 15. The syringe 10 is further provided with a needle cover comprising needle sheath 17 and rigid needle sheath cover 19. The rear end of the plunger rod 80 may be seen to define a thumb pad 82, and the forward end of the plunger has a toe 84 arranged for receipt within rear cavity 13 of syringe plunger 18.

Mounting to the rear part of housing 20, there is provided a handle comprising a handle body 30 and an opposing pair 32, 34 of handle arms. The rear part of handle body 30 defines locating arrangement 36 arranged for locating receipt of wings 22 on housing 20. Once mounted to the housing 20, the handle 30 is therefore not rotatable relative to the housing.

The forward end of housing 20 is arranged for reversible receipt of a removable cap 40, 50. The removable cap comprises a first cap body part 40 in the form of a sleeve; and second cap body part 50 in the form of a plug arranged for receipt by the first cap body part 40. A connector in the form of needle cover gripper 56, which has a cage-like (or 'flower') structure is further provided to the removable cap 40, 50.

Further details of the removable cap 40, 50 and needle cover gripper 56 are shown by reference to FIGS. 3A, 3B, 4, 7A-G and 8.

Figure 3A:
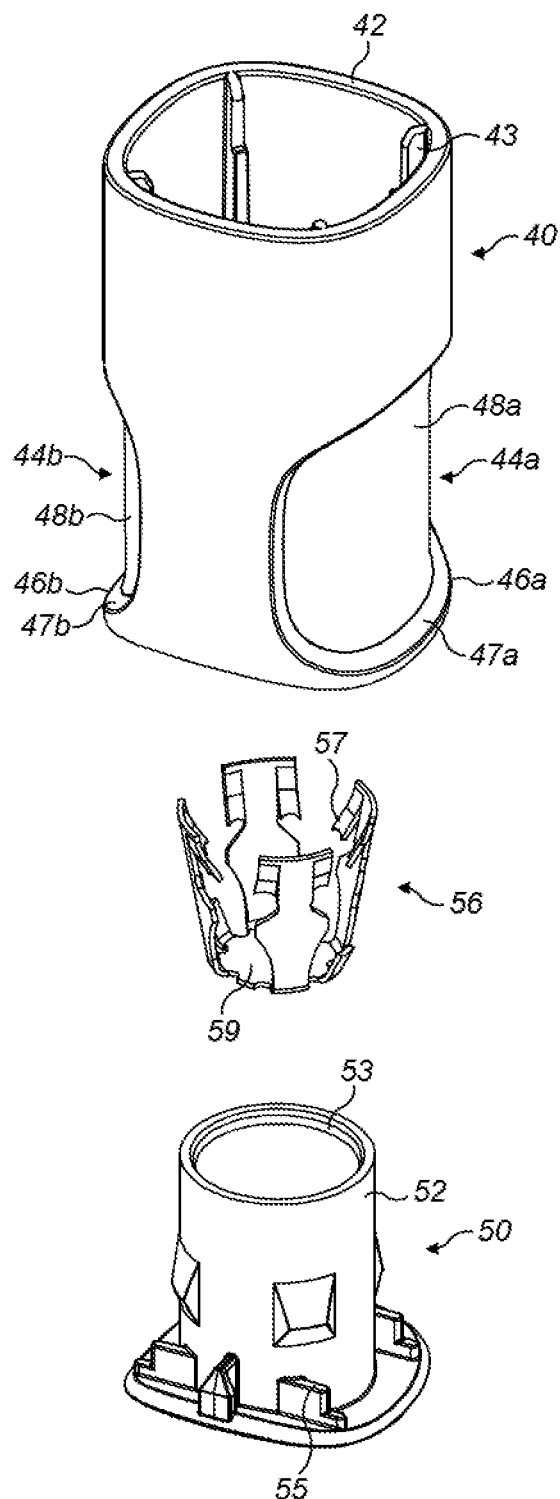
FIGS. 3A and 3B are exploded bottom and top views of a removable cap assembly of the injector of FIGS. 1B and 1B.
Figure 3B:
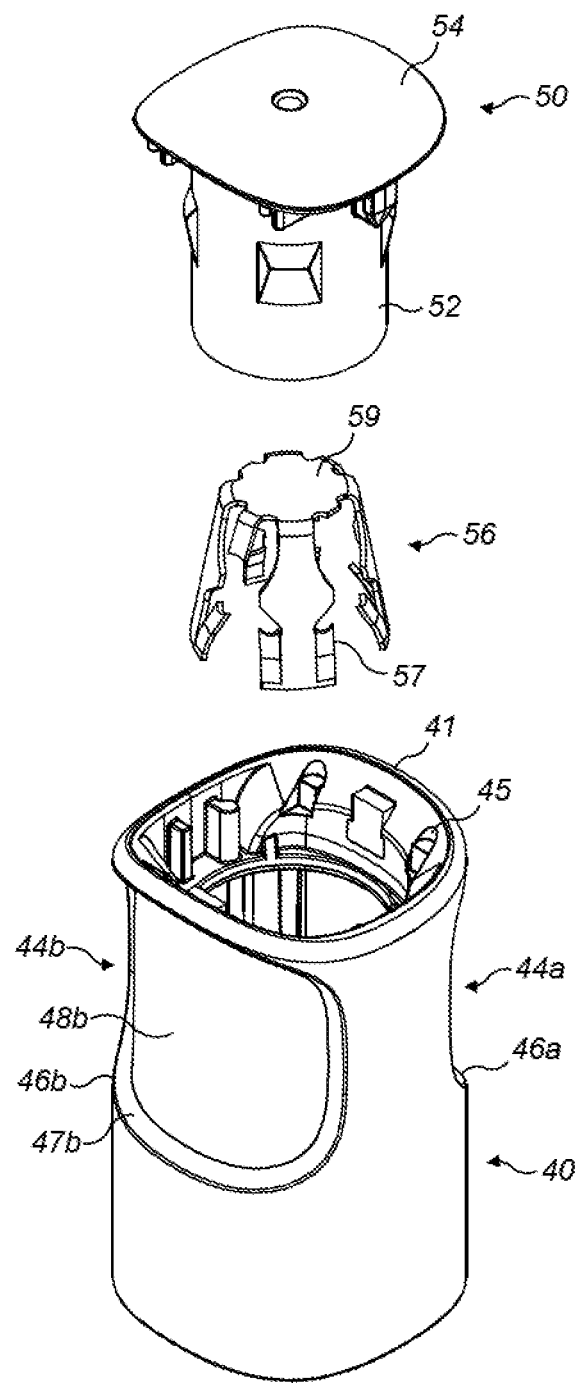

FIGS. 3A and 3B, in combination, show an exploded view of a cap assembly for the injector 1. Referring to FIGS. 3A and 3B, first cap body part 40 may be seen to have the form of a sleeve having forward 41 and rear 42 openings. The rear opening 42 may be seen to be provided with mating protrusions 43 arranged for mating receipt of collar 24 of the forward end of housing 20 (see FIG. 2). The first cap body part may be appreciated to define a generally rectangular cuboid profile having four generally rectangular cap body sides.

Second cap body part 50 may be seen to have the form of a plug defining an inner plug body/mating part in the form of a boss 52, the outer part of which is arranged for receipt by forward opening 41 of the sleeve form first cap body part 40. The inner well 53 of boss 52 defines a protruding pocket and is arranged for receipt of the connector 56 for gripping the needle cover 17/19 of the syringe 10.

Figure 4:
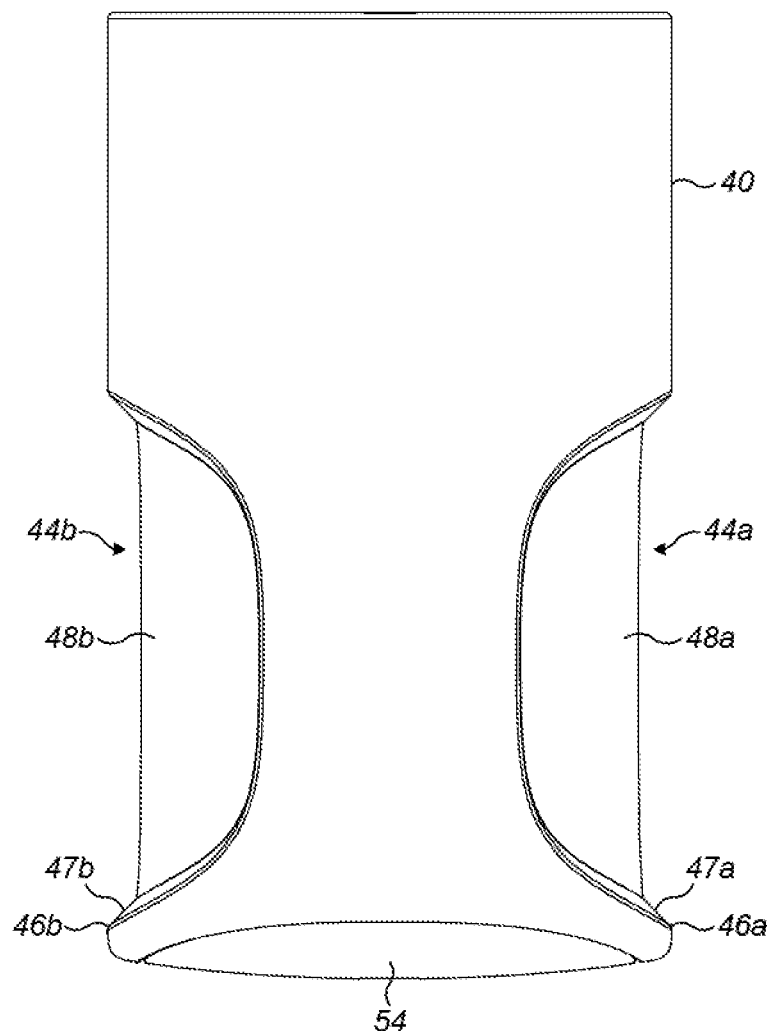
FIG. 4 is a side-on view of a removable cap of the injector of FIGS. 1A and 1B.

The plug form second body part also defines a plug top 54. On assembly of the first 40 and second 50 cap body parts, as shown at FIG. 4, the plug top 54 forms a cover for the forward opening 41 of the sleeve form first cap body part. In the plugged in configuration, locating pins 55 on the second plug form cap body part 50 interact with locating hollows 45 (e.g. in snap-fit fashion) on the first sleeve form cap body part 40. It will also be appreciated that on assembly, the connector 56 for gripping the needle cover 17/19 of the syringe 10 extends into the sleeve form first cap body part 40. In embodiments, the sleeve form first cap body part 40 receives the plug form second cap body part is snap-fit fashion.

Again referring to FIGS. 3A and 3B, needle cover gripper 56 in the form of a cage-like (or 'flower') structure and defining plural gripping elements 57 arranged about a central hub 59 is further provided to the second cap body part 50. Such gripping elements 57 are arranged for gripping of the rigid needle sheath cover 19 on removal of the removable cap 40, 50 such that removal of the cap 40, 50 also results in removal of the rigid needle sheath cover 19 and needle sheath 17 enclosed thereby, and hence, unsheathing of the needle tip 15.

Figure 7A:
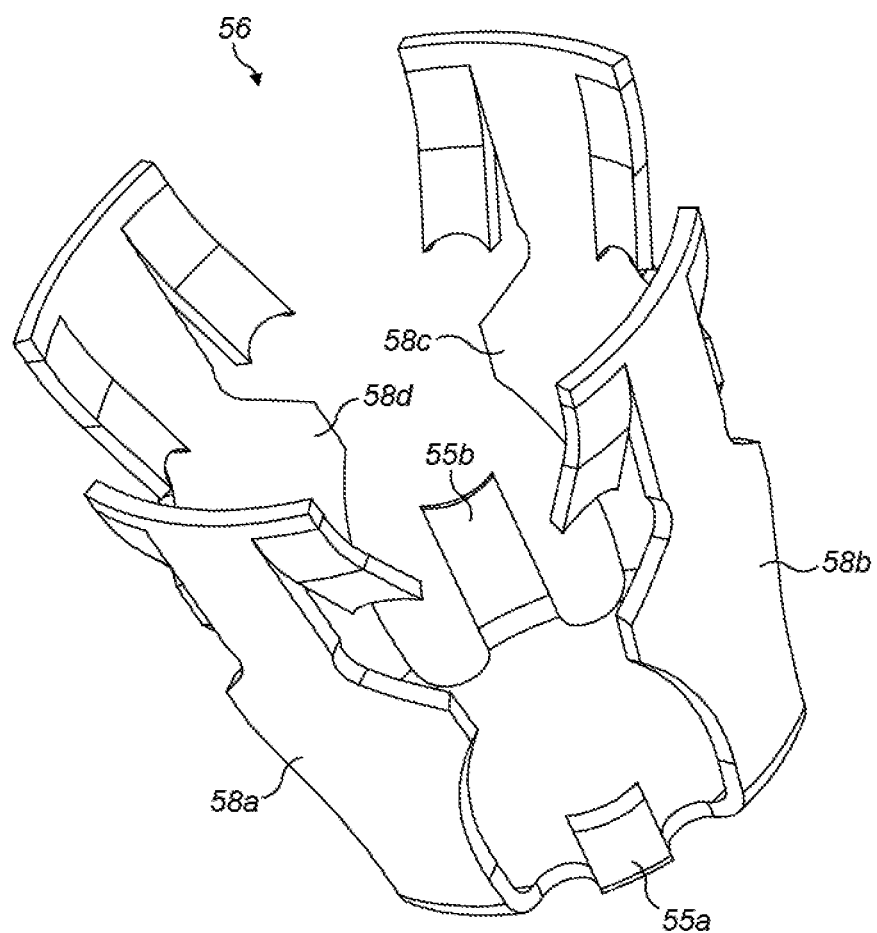
FIGS. 7A to 7G are various views of a connector for connecting the needle cover to the removable cap in the assembly of FIG. 3.
Figure 7B:
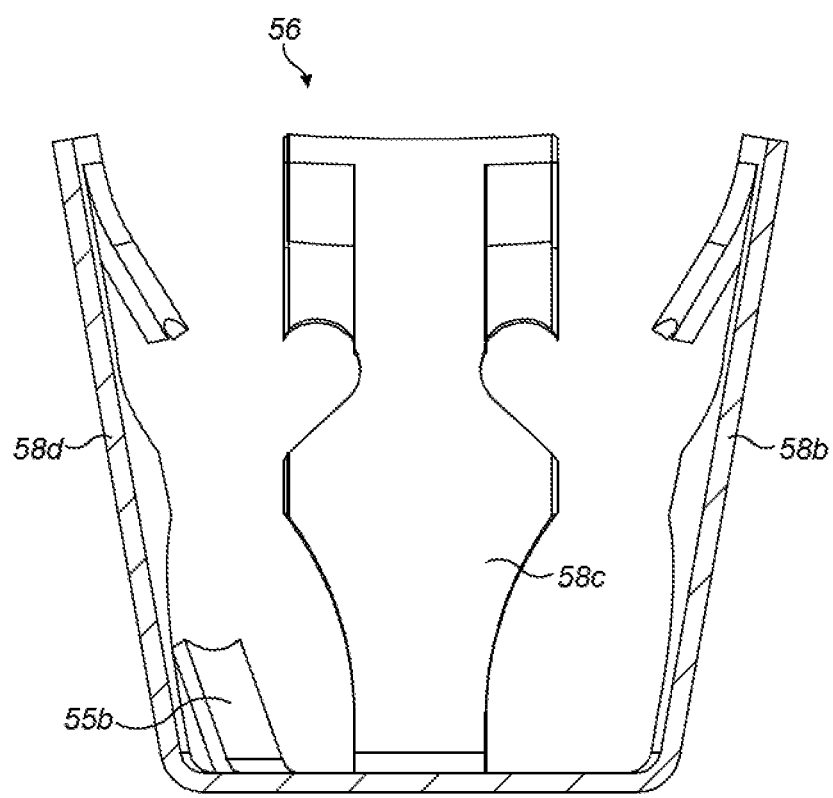
Figure 7C:
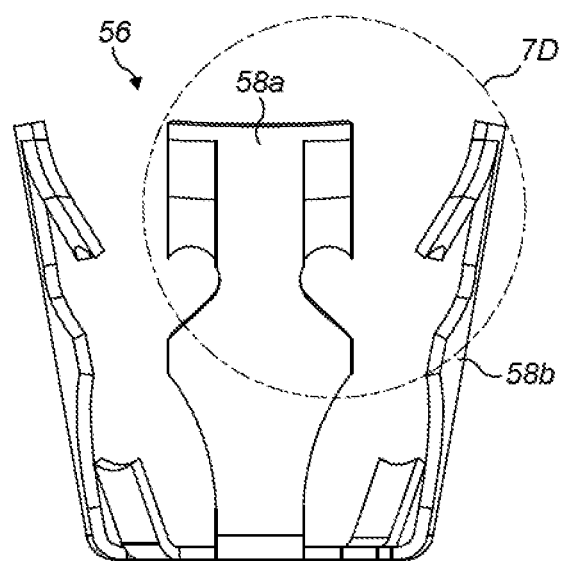
Figure 7D:
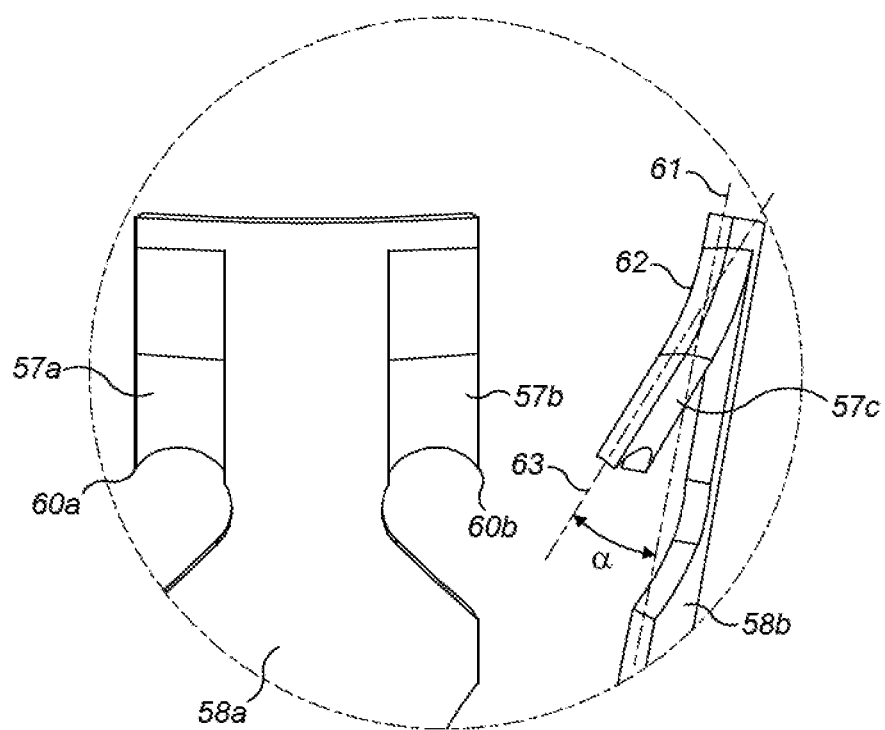
Figure 7E:
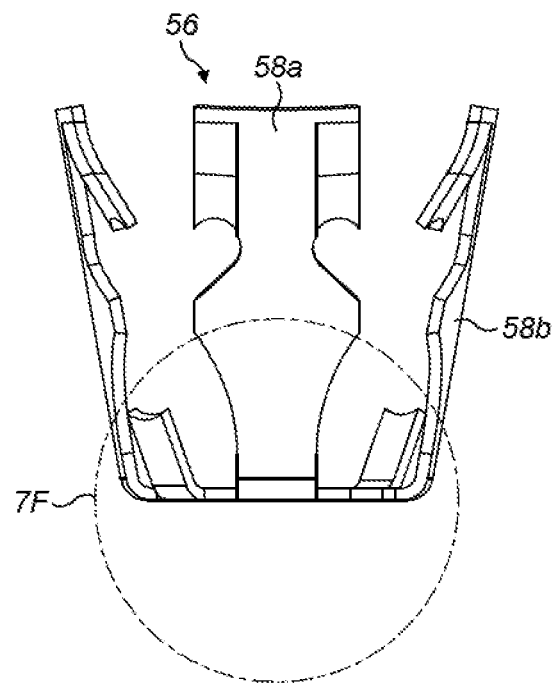
Figure 7F:
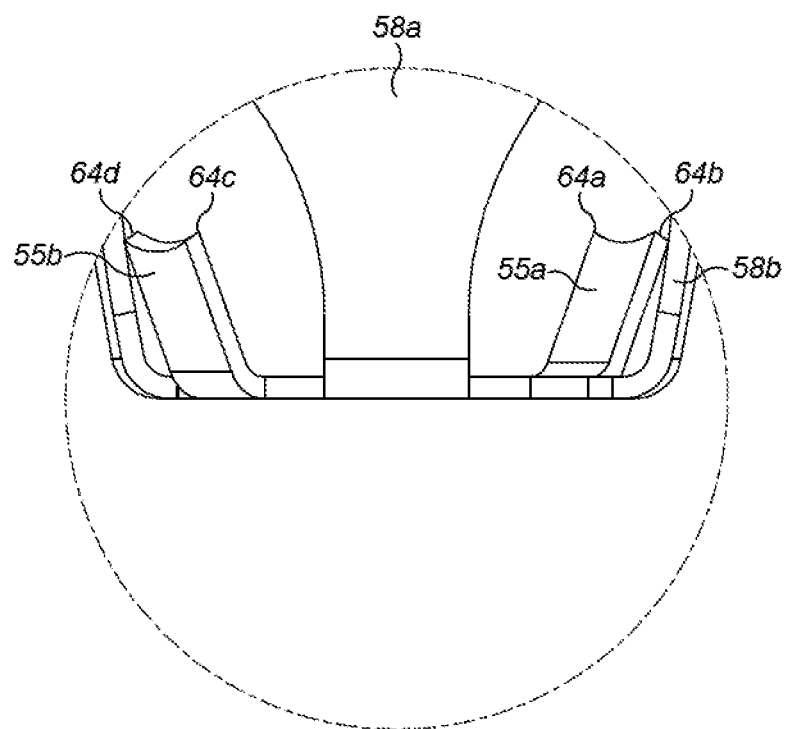
Figure 7G:
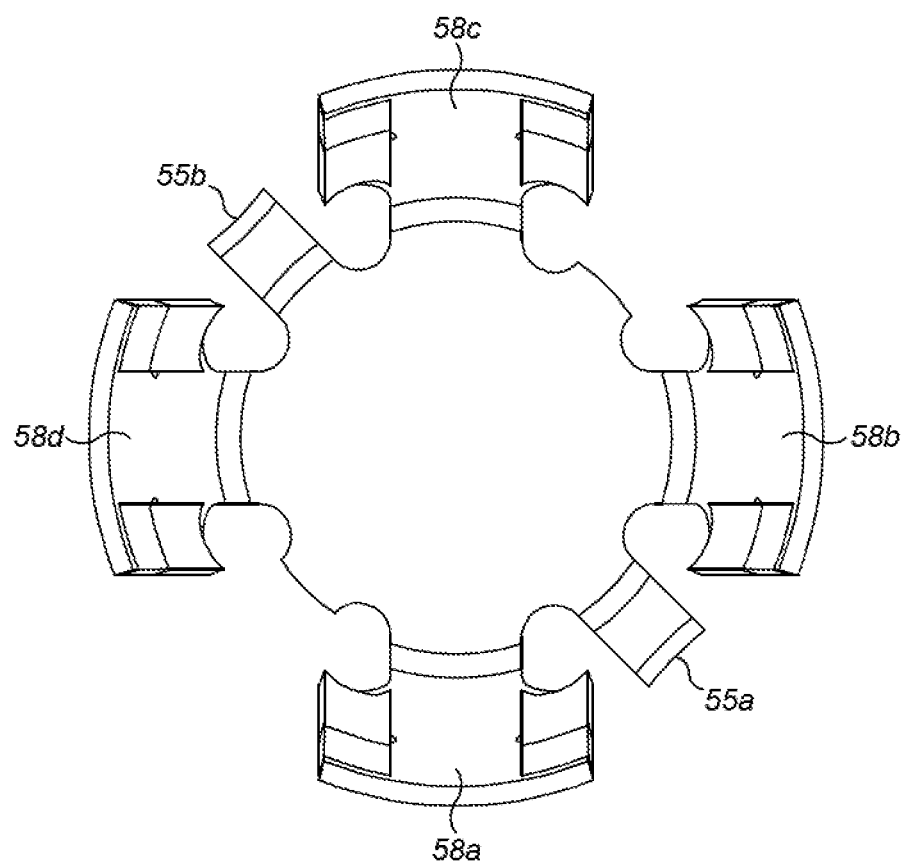

FIGS. 7A to 7G show various views of the connector/needle cover gripper 56. As shown in FIG. 7G, the connector 56 includes the first plurality of legs 58*a*-58*d* spaced symmetrically away from one another. The connector 56 is made, in certain embodiments, from a thin sheet of stainless steel, formed by a tool that bends the first legs into angles with respect to the horizontal. Such configuration and the elastic nature of these legs aid in securing the needle cover 17 and/or rigid needle sheath cover 19 to the removable cap 50. The needle cover 17 and/or rigid needle sheath cover 19 and the removable cap 50 are also secured together through upper, internally facing barbs 57*a*-57*c* protruding from the first legs 58*a*-58*d*. The upper, internally facing barbs 57*a*-57*c* include tips 60*a*-60*b* that point toward the forward end of the connector 56 (i.e. the needle tip 15 end). As illustrated in FIGS. 7C and 7D, these barbs are spaced about the perimeter of the connector 56 near its proximal end, with each of the first legs (e.g. 58*a*) having two internally facing barbs (e.g. 57*a*-57*b*), and each barb containing a pair of barb tips (e.g. 60*a*-60*b*). In some embodiments, the upper, internally facing barbs 57*a*-57*c* are concaved as shown in FIGS. 7A to 7E. These barbs are shaped to engage the needle cover 17 and/or rigid needle sheath cover 19 when the needle cover 17 and/or rigid needle sheath cover 19 is fitted within the connector 56. More specifically, the barb tips (e.g. 60*a* and 60*b*) apply opposing force with respect to one another when they engage the needle cover 17 and/or rigid needle sheath cover 19 as the barb tips 60*a*, 60*b* are disposed at two ends of a concaved surface (e.g. upper, internally facing barbs 57*a*-57*c*). In some embodiments, the upper, internally facing barbs 57*a*-57*c* are disposed at an angle with respect to the body of the first legs 58*a*-58*d*. This is more particularly shown in FIG. 7D. Such configuration may enhance the engagement between the needle cover 17 and/or rigid needle sheath cover 19 and the connector 56 as added protrusion (i.e., angled disposition of the barbs 57*a*-57*c* with respect to the first legs 58*a*-58*d*) allows the barb tips 60*a*-60*b* to more securely dig into the needle cover 17 and/or rigid needle sheath cover 19 when a user pulls the removable cap 40, 50 forwardly. As depicted in FIG. 7D, the longitudinal axis 61 of the upper portion 62 of the first legs 58*a*-58*d* is disposed at angle [alpha] with respect to the central axis 63 of the upper, internally facing barb 57*c*. The central axis 63 may be disposed between about 3 degrees to about 30 degrees with respect to the longitudinal axis 61 of the first legs 58*a*-58*d*.

As noted above, the connector 56 contains a second plurality of legs 55*a*-55*b* spaced symmetrically away from one another in the forward end of the connector 56. As shown in FIGS. 7E and 7F, each of the second plurality of legs contains lower, externally facing barb tips 64*a*-64*d* that point toward the rear end of the connector 56. These barbs engage a lower, interior portion of the removable cap 40, 50, thereby barbing the connector 56 to the removable cap 40, 50 in a manner similar to the connections between the upper, internally facing barb tips 57*a*-*c* and the needle cover 17 and/or rigid needle sheath cover 19 as described above. As the lower barbs 64*a*-64*d* extend proximally into the removable cap 50, these barbs 64*a*-64*d* prevent, in combination with the upper, internally facing barb tips 58*a*-58*d*, the removable cap 40, 50 from disengaging from the connector 56.

Figure 8:
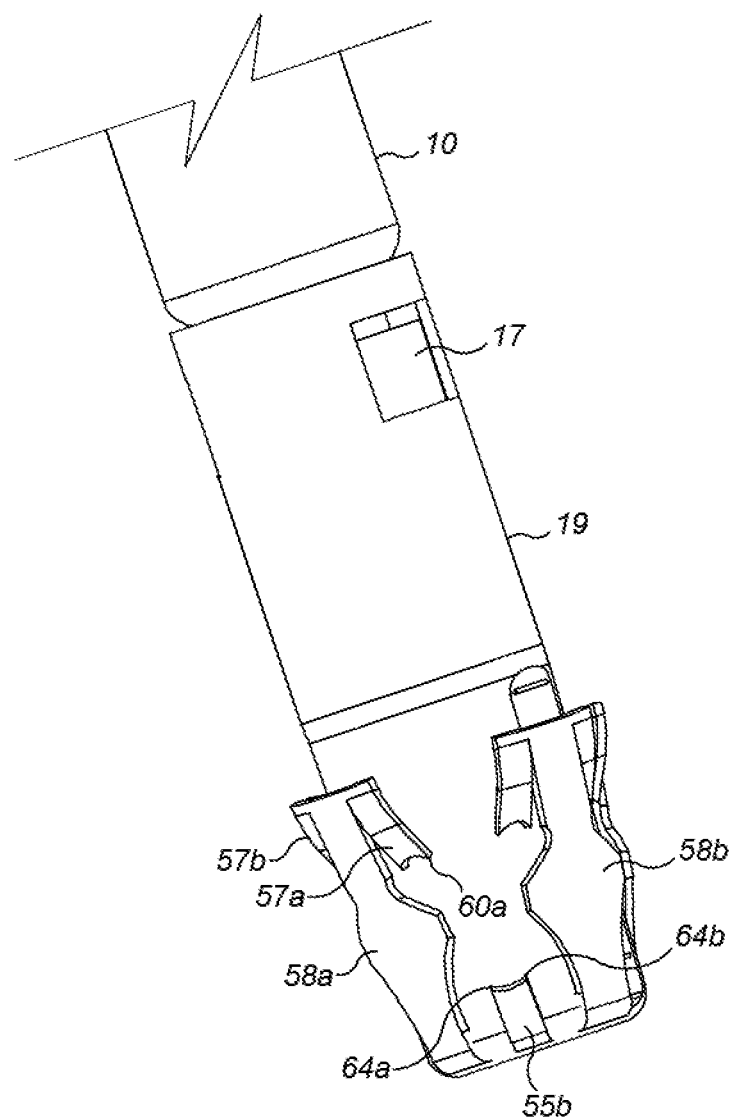
FIG. 8 is a perspective view showing how the connector of FIGS. 7A to 7G connects to a needle cover of a syringe.

FIG. 8 depicts an exemplary mating relationship between the needle cover comprising needle sheath 17 with rigid needle sheath cover 19 and the connector 56. The needle sheath 17 acts to sheath the needle (not visible) of the syringe 10. Barb tips 60*a*, 60*b* of barbs 57*a*, 57*b* engage the rigid needle sheath cover 19, as shown.

Figure 5A:
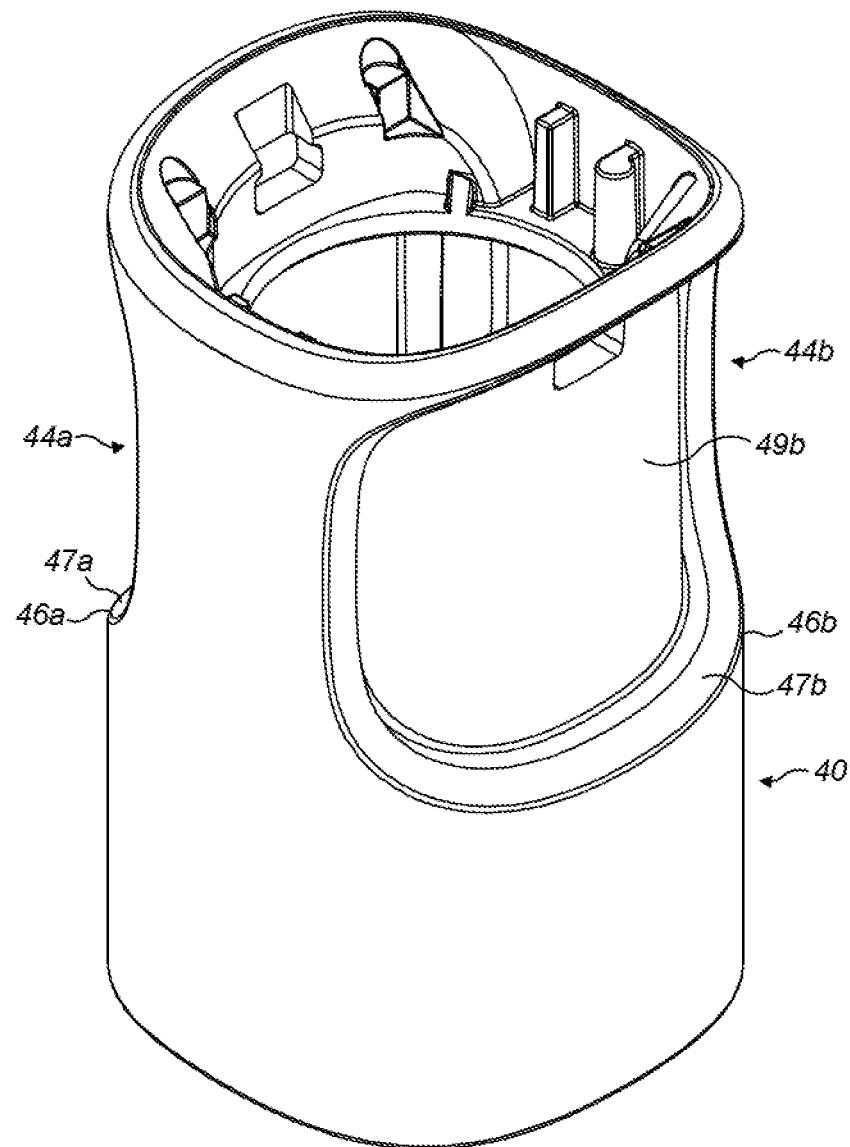
FIGS. 5A and 5B are perspective top and bottom views of the body of removable cap of FIG. 4 absent its flexible over-coating.
Figure 5B:
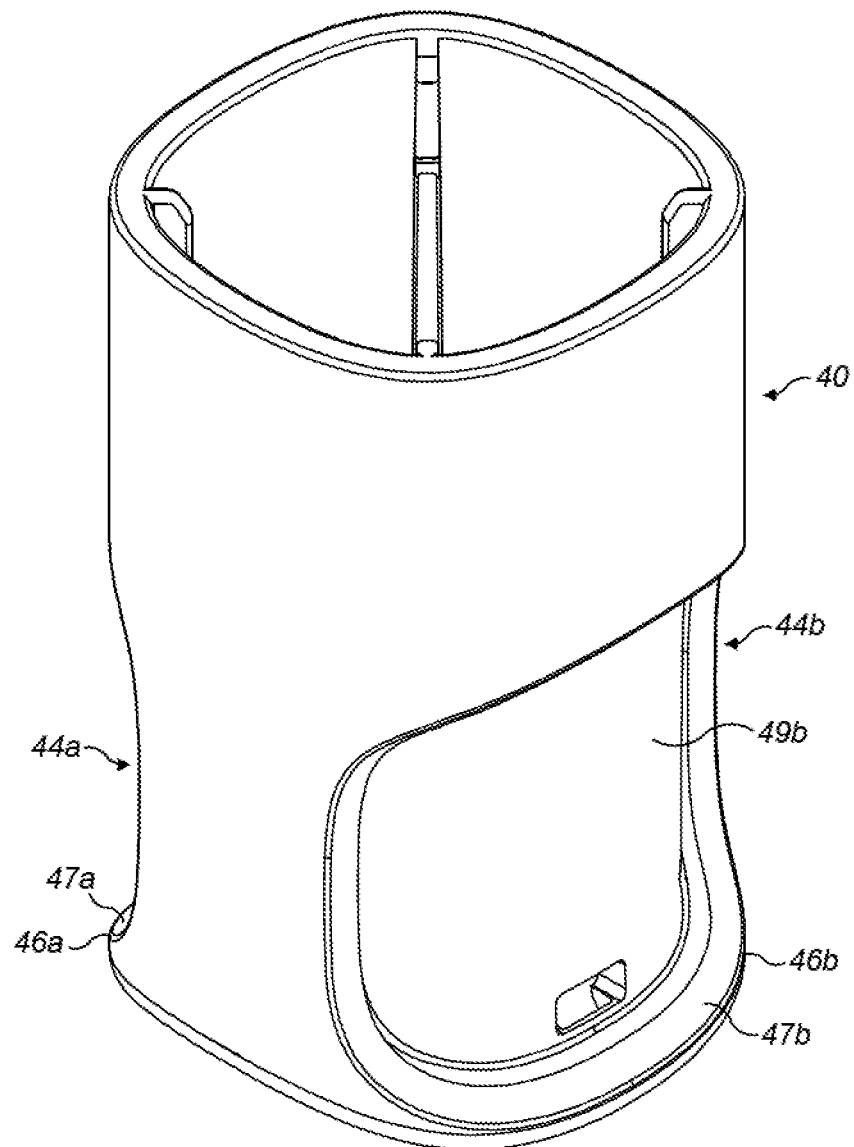

Referring again now to FIGS. 3A, 3B and 4, it may be seen that the sleeve form first cap body part 40 is provided with opposing pair 44*a*, 44*b* of recessed portions, wherein each recessed portion is bounded by a peripheral lip 46*a*, 46*b*. Each recessed portion 44*a*, 44*b* has an over-coating 48*a*, 48*b* of a material (e.g. a thermoplastic elastomer) that is more flexible than that of the generally rigid material (e.g. a thermoplastic polymer such as polypropylene or ABS/polycarbonate) from which the first cap body part 40 is comprised. FIGS. 5A and 5B show the first cap body part 40 prior to over-coating, and the recess base 49*b* (49*a*, not visible) of each recessed portion 44*a*, 44*b* to which the over-coating 48*a*, 48*b* is later applied may therefore be seen. It may be appreciated that each recess base 49*b* with over-coating 48*a*, 48*b* defines a profile that corresponds with a rectangular side of the first cap body part 40 but is recessed relative thereto. The over-coating 48*a*, 48*b* is provided as an over-moulding to the recess base 49*a*, 49*b*.

It may also be seen that each peripheral lip 46*a*, 46*b* of a recessed portion 44*a*, 44*b* defines a bank 47*a*, 47*b* that extends beyond the over-coating 48*a*, 48*b* of the recess base 49*b*. The bank 47*a*, 47*b* of each peripheral lip 46*a*, 46*b* rises up in angular fashion from the over-coating 48*a*, 48*b* of the recess base 49*b*. As may be seen with reference to FIG. 4, at least forward and rear bank portions 47*a*, 47*b* of the peripheral lip 46*a*, 46*b* rise up at an angle of about 45° to the surface of the over-coating 48*a*, 48*b* of the recess base 49*b*.

In embodiments, providing the cap as an assembly allows for ease of manufacture of the first cap body part 40 with its different moulded aspects, and thus removes the need for intricate mould details that would be required if these two different moulded aspects were formed using a single mould process. In embodiments, the first cap body part 40 is formed using a two shot injection process that bi-moulds from the inside and as a result discretely hides the injection points, for a cleaner finished part. In addition, provision of the second cap body part 50 allows for ease of manufacturing access by allowing for its assembly with the needle cage gripper 56 before that sub-assembly is mated with the first cap body part 40.

As shown at FIGS. 1A, 1B and 2, in the capped (e.g. 'pre-use') configuration, the removable cap 40, 50 is received by the housing 20 of injector 1 such that the opposing pair of recessed portions 44*a*, 44*b* on the first cap body part 40 line up with the opposing pair of handle arms 32, 34 of the handle.

The removable cap 40, 50 allows for ease of use to remove the needle cover 17, 19 from the needle 14 of the syringe 10. The recessed portions 44a, 44b with overcoatings 48a, 48b provide (e.g. non-slip) grip areas. The banks 47a, 47b of the peripheral lips 46a, 46b are suitably arranged to follow the curvature of the fingers and thumb of a user when the cap 40, 50 is held in a pinch grip or partial power grip.

In embodiments, the cap 40, 50 is formed by a bi-moulding process. In embodiments, the over-coatings 48a, 48b provided to the recessed portions 44a, 44b comprise a thermoplastic elastomer material that provides a non-slip grip area and the banks 47a, 47b of the peripheral lips 46a, 46b comprise a rigid thermoplastic polypropylene (or alternatively, ABS/polycarbonate) material that offers a solid surface to locate against. Such arrangement allows for intuitive orientation of the fingers and thumb of the user and allows greater ease of removal of the cap 40, 50 with needle cover 17, 19 from the housing 20.

In embodiments, and as shown at FIGS. 1A, 1B and 2, the removable cap 40, 50 is received by the housing 20 such that the opposing pair of recessed portions 44a, 44b on the first cap body part 40 line up with the opposing pair of handle arms 32, 34 of the handle. This arrangement of cap 40, 50 to housing 20 ensures that there is less stress placed on the user's wrist when removing the cap 40, 50, and allows the hand to naturally align with the finger grips when holding the injector 1 in either a pinch grip or partial power grip. This provides more options for the patient to remove the cap 40, 50 from the housing depending upon the level of hand dexterity.

Figure 6A:
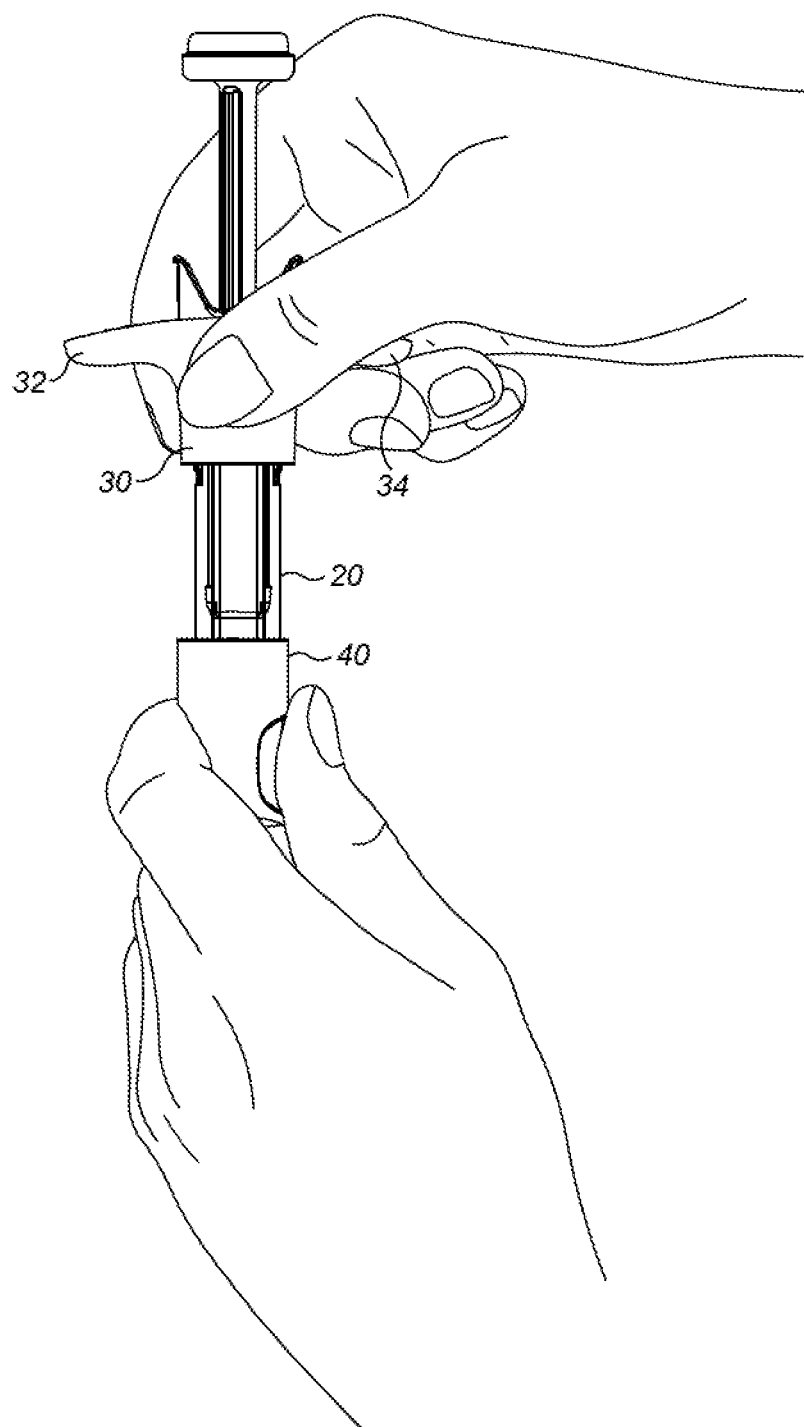

FIG. 6A shows a first stage ('cap on') in removal of the cap 40, 50 from the housing 20 of the injector 1 of FIGS. 1A, 1B and 2 by means of a partial power grip. The thumb and fingers of a user's first hand partially power grip the injector 1 by means of arms 32, 34 of the handle 30. The thumb and index finger of a user's second hand grip the cap 40, 50 by means of recessed portions 44a, 44b with (e.g. nonslip) over-coatings 48a, 48b. The banks 47a, 47b of the peripheral lips 46a, 46b follow the curvature of the index finger and thumb of a user and offer a solid surface for the user's thumb and index finger locate against. Ease of cap removal is thus, enabled.

Figure 6B:
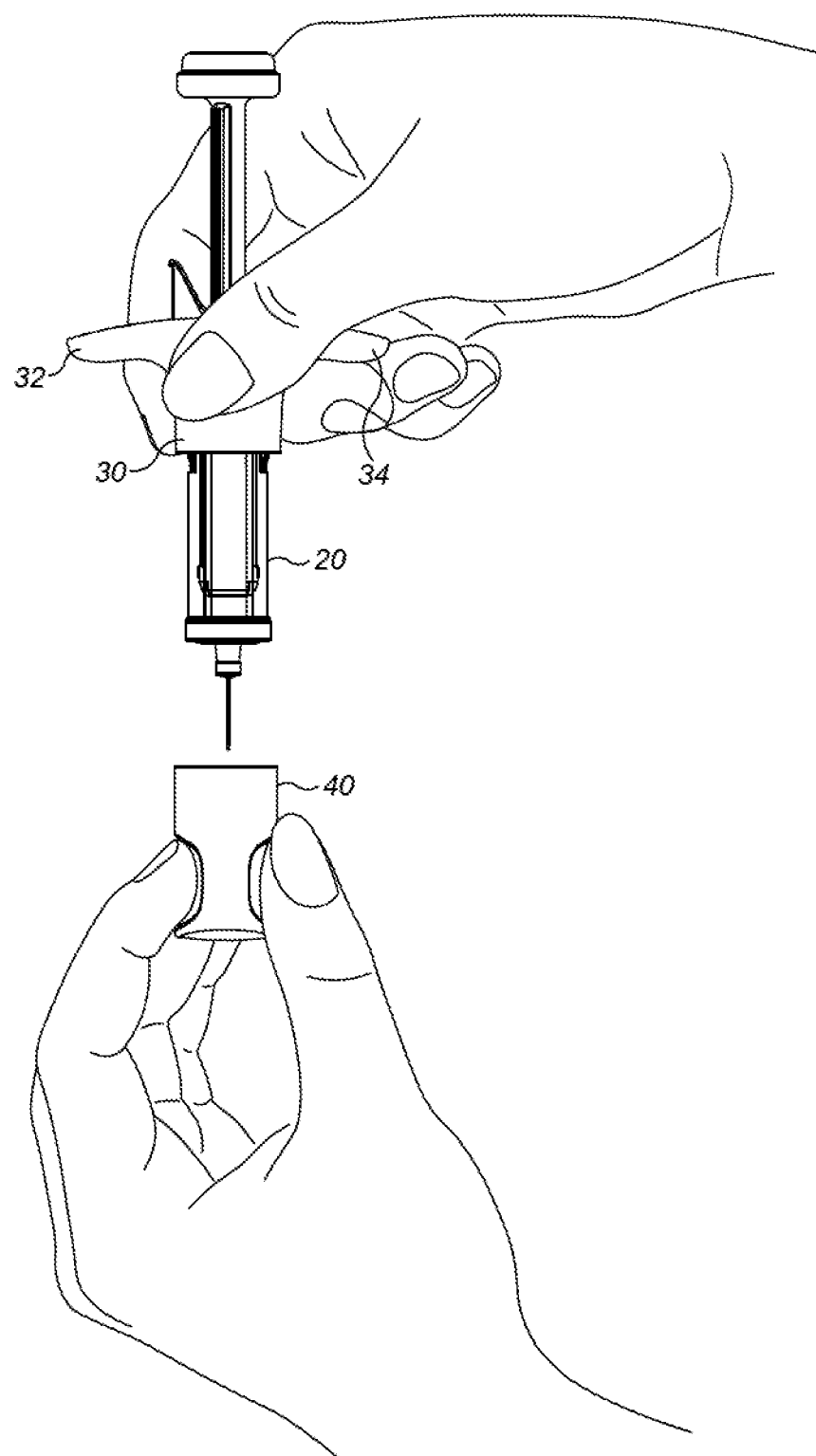

FIG. 6B shows a second stage (cap off) in removal of the cap 40, 50 from the housing 20 of the injector 1 of FIGS. 1A, 1B and 2 by means of a pinch grip. The thumb and fingers of a user's first hand grip the injector 1 by means of arms 32, 34 of the handle 30. The thumb and index finger of a user' second hand pinch grip the cap 40, 50 by means of recessed portions 44a, 44b with (e.g. nonslip) over-coatings 48a, 48b. The banks 47a, 47b of the peripheral lips 46a, 46b follow the curvature of the index finger and thumb of a user and offer a solid surface for the user's thumb and index finger locate against. Ease of cap removal is thus, enabled.

The injector of FIGS. 1A, 1B and 2 is arranged for manual actuation. Having removed the cap 40, 50 and needle cover 17/19, the user places the tip 15 of needle 14 at the injection site. The user grips the injector 1 by means of arms 32, 34 of the handle, inserts the needle at an injection site, and applies drive force to the plunger rod 80, which transfers drive force to the plunger 18 of the syringe 10 for axial movement thereof within the syringe barrel 12. Such movement of the plunger 18 results in the plunged driving of the liquid drug from the syringe barrel 12 to the hollow needle 14 for dispensing at the injection site via the needle tip 15 thereof.

Figure 9:
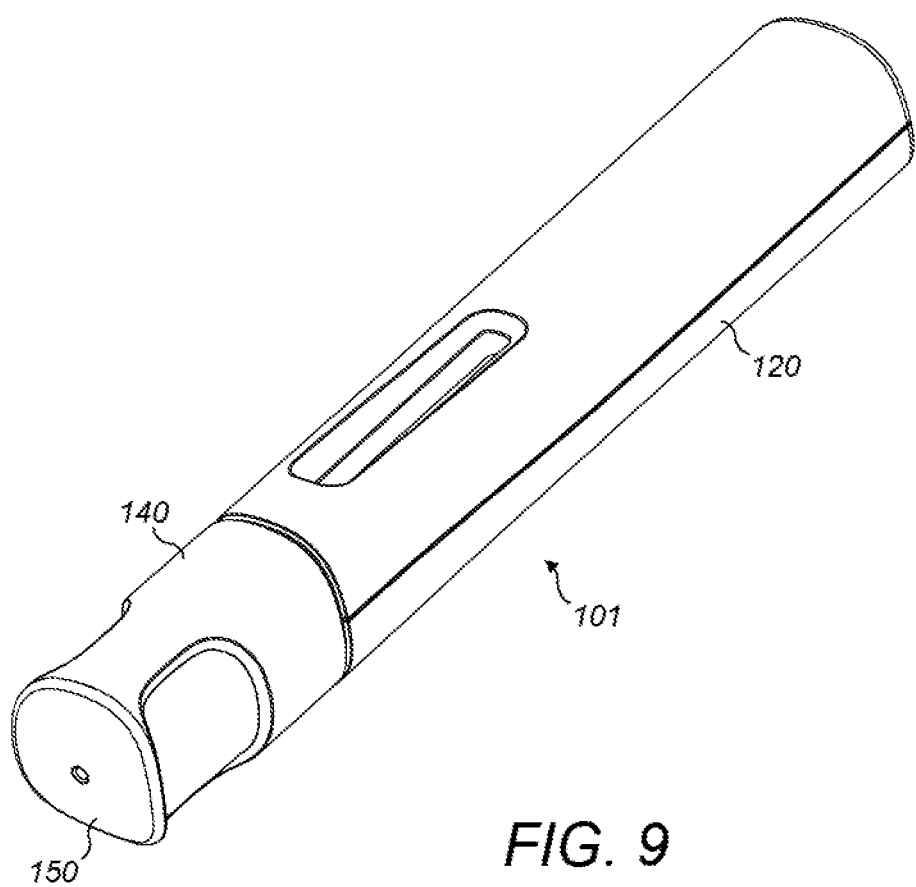
FIG. 9 is a perspective view of a second injector herein in the 'pre-use' position with a removable cap thereof in docked receipt by a housing thereof.
Figure 10:
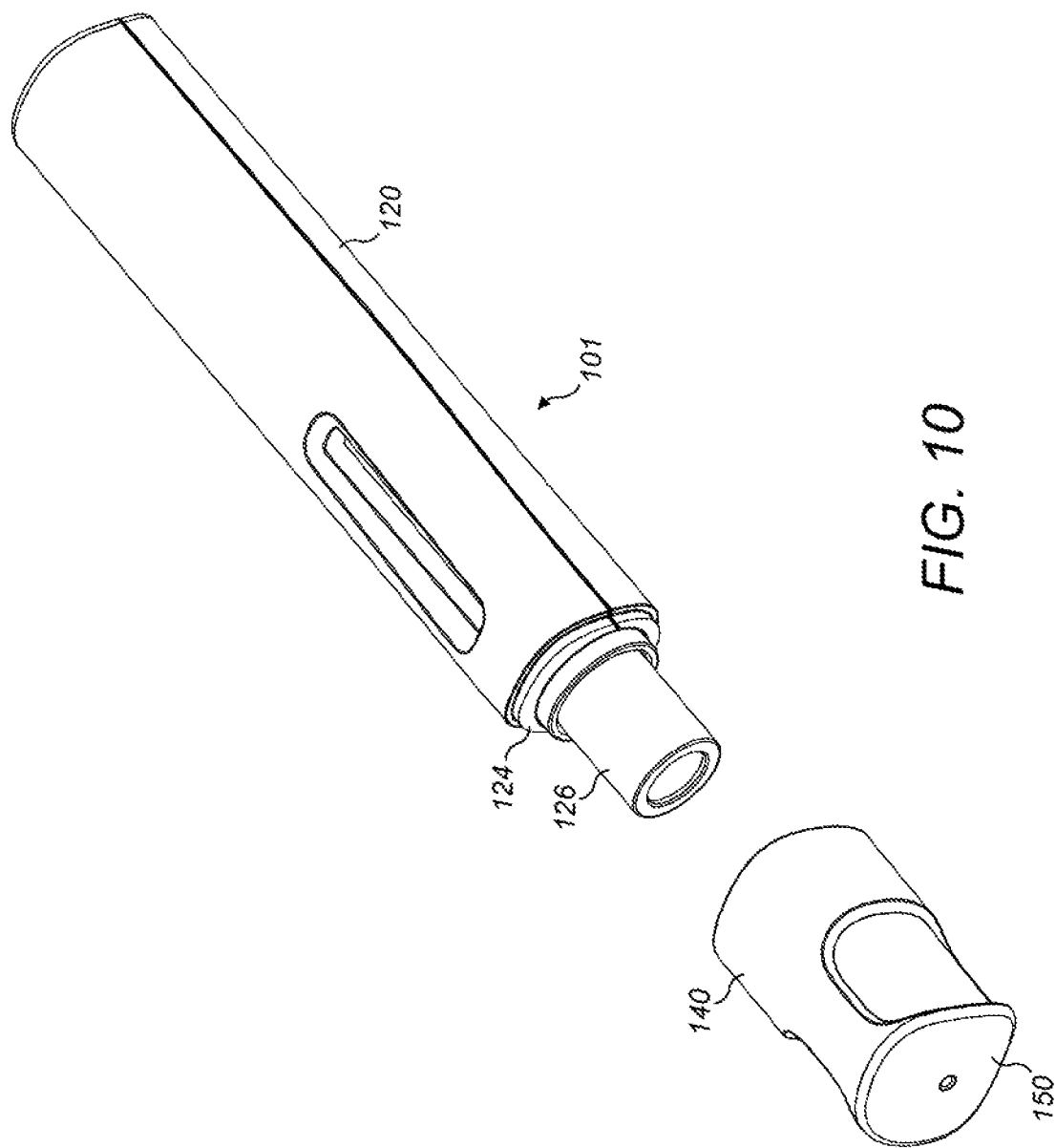
FIG. 10 is a perspective view of the second injector of FIG. 9 in the 'ready to use' position with the removable cap removed from the housing thereof.
Figure 11:
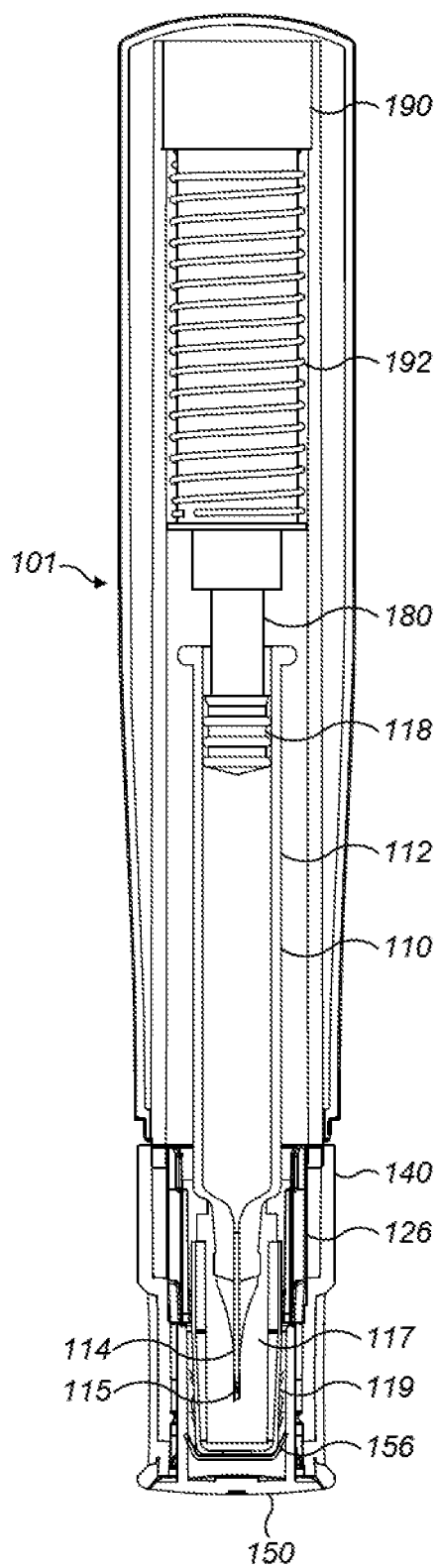
FIG. 11 is a sectional view of the second injector of FIGS. 9 and 10.

FIGS. 9 to 11 show aspects of an auto-injector 101 herein, which is arranged for use with a syringe with needle cover that contains a liquid drug formulation. FIG. 9 shows the auto-injector 101 in a capped (pre-use) configuration and FIG. 10 shows the auto-injector 101 in an un-capped (ready to use) configuration. The auto-injector 101 comprises a super-ellipse (square with soft-radiused sides and corner radii) form housing 120, which is arranged for receipt of the syringe with needle cover and is sized and shaped for this purpose.

The syringe 110 with needle cover 117, 119 for use with the auto-injector 101 of FIGS. 9 to 11 is identical in form to that syringe 10 with needle cover 17, 19 employed in the manual injector of FIGS. 1A to 6B, and for succinctness if therefore not described again in detail.

The forward end of housing 120 of the auto-injector is arranged for reversible receipt of a removable cap comprising a first cap body part 140 in the form of a sleeve; and second cap body part 150 in the form of a plug arranged for receipt by the first cap body part 140. A connector in the form of needle cover gripper 156, which has a cage-like (or 'flower') structure is further provided to the removable cap 140, 150.

The first cap body part 140, second cap body part 150 and needle cover gripper 156 are generally identical in design form to the first cap body part 40, second cap body part 50 and needle cover gripper 56 employed in the manual injector of FIGS. 1A to 6B, and for succinctness these parts are therefore not described again in detail.

With reference to FIG. 10, the first cap body part 140 has mating protrusions provided at its rear opening (details not visible in FIG. 10, but identical to the mating protrusions 43 provided at the rear opening 42 of first cap body part 40 of the manual injector of FIGS. 1A to 6B) arranged for mating receipt of collar 124 of the forward end of housing 120. The first cap body part 140 may be appreciated to define a generally rectangular cuboid profile having four generally rectangular cap body sides.

Also provided at the forward end of housing 120 is a sleeve actuator 126, which is light spring mounted relative to the housing 120 and may be depressed to overcome the light return force of the spring. A rear end of the sleeve actuator 126 is coupled to an actuating mechanism 190, which allows for release of an automatically operable drive transfer element 180 for transferring axial drive to the plunger 118 of the syringe 110; and an energy store in the form of a drive spring 192 for providing drive energy to the drive transfer element 180.

Figure 12A:
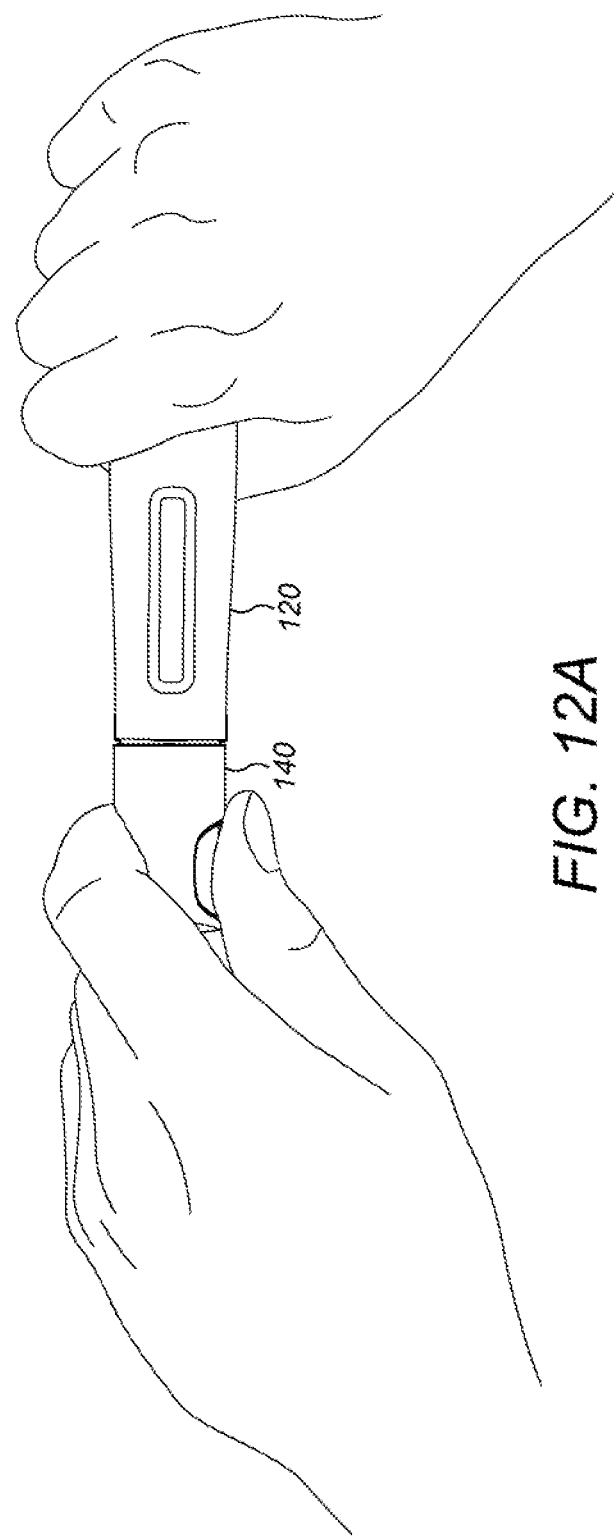
Figure 12B:
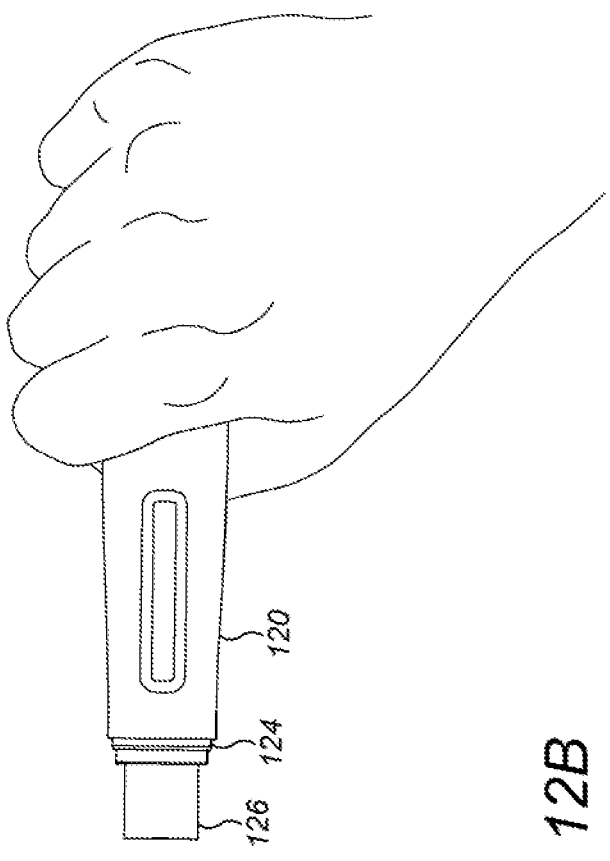
Figure 12B:

FIG. 12A shows a first stage ('cap on') in removal of the cap 140, 150 from the housing 120 of the auto-injector 101 of FIGS. 9 to 11. The thumb and fingers of a user's first hand power grip the auto-injector 101 by means of the rearward part of housing 120. The thumb and index finger of a user's second hand partially power grip the cap 140, 150, which has recessed portions with over-coatings (identical to the recessed portions 44a, 44b with (e.g. nonslip) over-coatings 48a, 48b of the injector 1 of FIGS. 1 to 6B), for proving grip and peripheral lips with banks (again identical to the peripheral lips 46a, 46b with banks 47a, 47b of the cap 40, 50 of the injector 1 of FIGS. 1 to 6B), which follow the curvature of the index finger and thumb of a user and offer a solid surface for the user's thumb and index finger locate against. Ease of cap removal, as shown at FIG. 12B in the second stage of the process is thus, enabled.

Figure 13A:
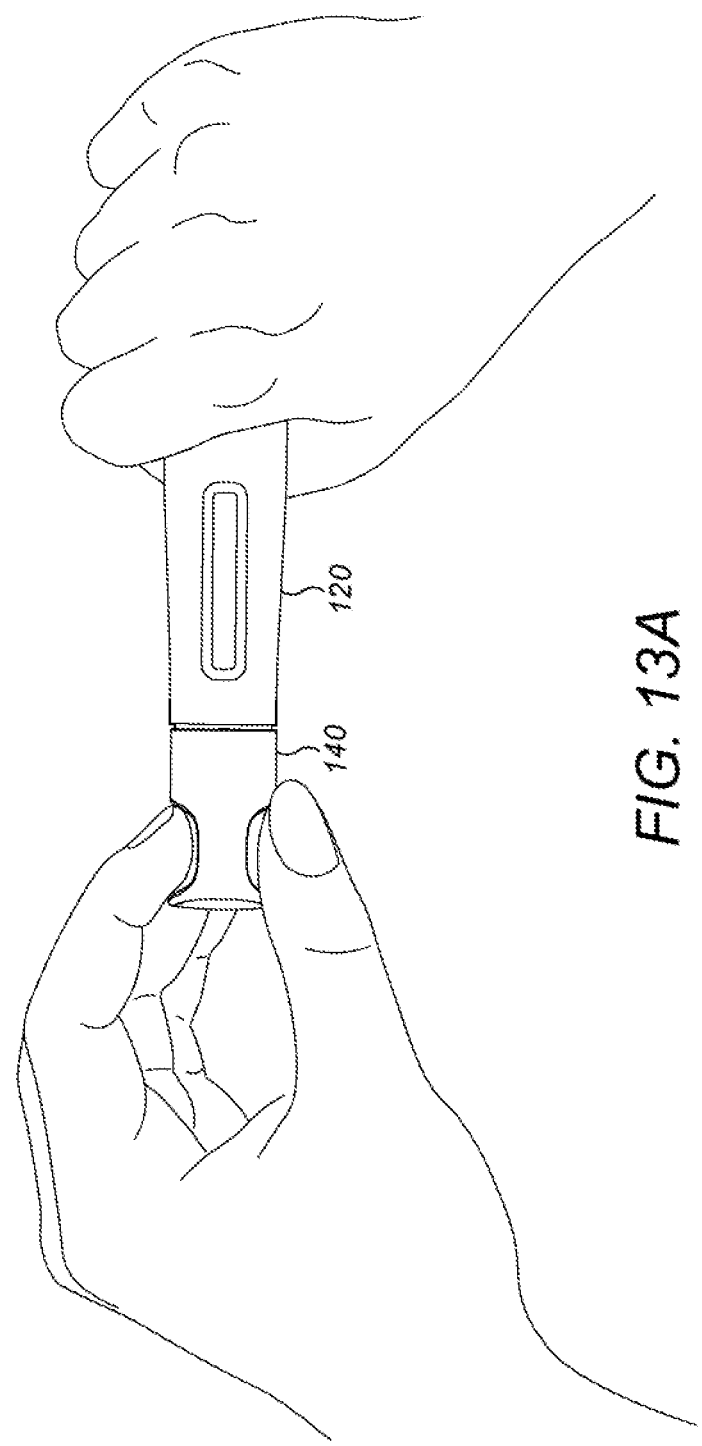
Figure 13B:
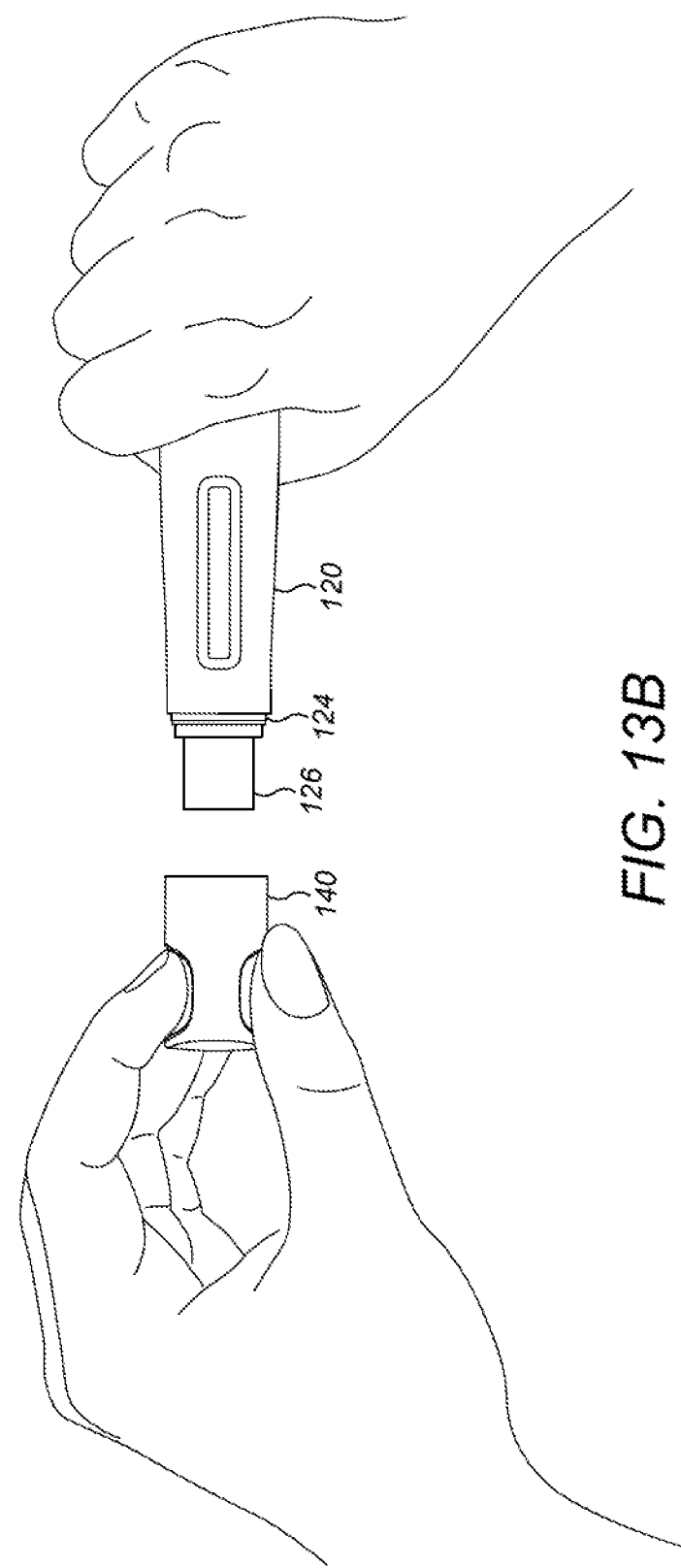

FIG. 13A shows a first stage ('cap on') in removal of the cap 140, 150 from the housing 120 of the auto-injector 101 of FIGS. 9 to 11. The thumb and fingers of a user's first hand power grip the auto-injector 101 by means of the rearward part of housing 120. The thumb and index finger of a user's second hand pinch grip the cap 140, 150, which has recessed portions with over-coatings (identical to the recessed portions 44a, 44b with (e.g. nonslip) over-coatings 48a, 48b of the injector 1 of FIGS. 1 to 6B), for proving grip and peripheral lips with banks (again identical to the peripheral lips 46a, 46b with banks 47a, 47b of the cap 40, 50 of the injector 1 of FIGS. 1 to 6B), which follow the curvature of the index finger and thumb of a user and offer a solid surface for the user's thumb and index finger locate against. Ease of cap removal, as shown at FIG. 13B in the second stage of the process is thus, enabled.

During a cap 140, 150 removal and/or cap 140, 150 replacement process, the user orients the injector 101 to a position most comfortable for them, particularly in view of any impaired manual dexterity that they may be coping with. Thus, the injector 101 may be oriented horizontally, vertically or at any angular orientation.

The injector of FIGS. 9 to 13A is arranged for automatic actuation. Having removed the cap 140, 150 and with it the needle cover 117/119, the user places the forward end of actuator sleeve 126 at the injection site. The user applies sufficient downward force to the actuator sleeve 126 to move it backwards and to thereby reveal the needle for insertion at the injection site, and subsequently to trigger release of the actuating mechanism 190, which releases the drive spring 192 to provide drive force via drive transfer element 180 to the plunger 118 of the syringe 110 for axial movement thereof within the syringe barrel 112. Such movement of the plunger 118 results in the plunged driving of the liquid drug from the syringe barrel 112 to the hollow needle 114 for dispensing at the injection site via the needle tip 115 thereof.

The injector herein is suitable for the injected delivery of drug, particularly for the treatment and/or prophylaxis of a number of diseases, disorders or conditions, including infections (viral, e.g. HIV infection, bacterial, fungal and parasitic); endotoxic shock associated with infection; inflammatory diseases/autoimmunity such as osteoarthritis, rheumatoid arthritis, psoriatic arthritis, systemic lupus erythematosus (SLE), ankylosing spondilitis, COPD, asthma, Alzheimer's Disease, Crohn's disease, ulcerative colitis, irritable bowel syndrome and psoriasis; immune mediated inflammatory disorders of the central and peripheral nervous system such as multiple sclerosis and Guillain-Barr syndrome; graft-versus-host disease; organ transplant rejection; pain; cancer (including solid tumours such as melanomas, hepatoblastomas, sarcomas, squamous cell carcinomas, transitional cell cancers, ovarian cancers and hematologic malignancies, acute myelogenous leukaemia, chronic myelogenous leukemia, gastric cancer and colon cancer); congenital disorders, e.g. cystic fibrosis and sickle cell anaemia; growth disorders; epilepsy; treatment of infertility; heart disease including ischaemic diseases such as myocardial infarction as well as atherosclerosis and intravascular coagulation; bone disorders such as osteopenia and osteoporosis; and metabolic/idiopathic disease, e.g. diabetes.

In embodiments, the syringe of the injector herein contains a liquid drug formulation, which is designed for refrigerated rest (e.g. at from 2-8° C.) and for injected delivery at room temperature (e.g. at or about 18-30° C.). In embodiments, the viscosity of the liquid drug formulation is less than 120 mPa·s (120 centipoise), in embodiments less than 100 mPa·s (100 centipoise) at a delivery temperature of 20° C.

Appropriate drugs may thus be selected from biologically active agents, including chemical entities, polysaccharides, steroids and, especially, naturally occurring and recombinant proteins, including glycoproteins, polypeptides and oligopeptides and polymeric derivatives thereof. Particular proteins, polypeptides and oligopeptides include hormones, such as insulin, epinephrine, norepinephrine, adrenocorticotrophin, somatotropin, erythropoietin and oxytocin; cytokines, such as lymphokines, chemokines and interleukins and receptors therefor, e.g. interleukin (IL)-1α, IL-1β, IL-1R, IL-2, IL-3, IL-4, IL-5, IL-6, IL-13, IL17, interferon (IFN)-α, IFN-β, IFN-γ, granulocyte monocyte colony stimulating factor, tumour necrosis factor-α; growth factors, such as nerve growth factor and platelet-derived growth factor; enzymes, such as tissue plasminogen activator; and, especially, immunoglobulins. Immunoglobulins include whole antibodies and functionally active fragments and/or derivatives thereof, for example polyclonal, monoclonal, recombinant, multi-valent, mono- or multi-specific, humanised or chimeric antibodies, single chain antibodies, Fab fragments, Fab' and F(ab')$_2$ fragments. Polymeric derivatives of such proteins, polypeptides and oligopeptides include derivatives formed between the protein, polypeptide or oligopeptide and a naturally occurring or synthetic polymer, e.g. a polysaccharide or a polyalylklene polymer such as a poly(ethyleneglycol) [PEG] or derivative thereof, e.g. methoxypoly (ethyleneglycol) [mPEG]. Particular agents include growth hormones and hormones for the treatment of infertility. Other particular agents are for the treatment of epilepsy such as brivaracetam and seletracetam.

The injector device herein has been found to be of particular utility where the drug is an immunoglobulin or a fragment thereof, especially a PEGylated or mPEGylated antibody fragment.

The liquid drug formulations herein are typically aqueous formulations, which comprise the drug in solution and additionally other optional formulation components, which may include buffers (e.g. lactate, acetate), NaCl, and pH modifiers (e.g. NaOH).

In embodiments, the injector herein is of utility wherein the concentration of the drug (e.g. a therapeutic biologic type drug) in the liquid drug formulation is quite high. In particular, where the drug is a pegylated antibody the auto-injector device has been found to be of particular utility wherein the concentration of the drug is greater than 100 mg/ml, particularly greater than 150 mg/ml such as 200 mg/ml.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented. Examples of changes, substitutions, and alterations are ascertainable by one skilled in the art and could be made without departing from the scope of the information disclosed herein. All references cited herein are incorporated by reference in their entirety and made part of this application.

The application of which this description and claims form part may be used as a basis for priority in respect of any subsequent application. The claims of such subsequent application may be directed to any feature or combination of features described herein. They may take the form of product, method or use claims and may include, by way of example and without limitation, one or more of the following claims.

The invention claimed is:

1. A cap for an injector comprising a syringe with a needle cover, said cap comprising
a cap body defining an inner and outer cap body;
provided to said inner cap body, a metal connector defining plural needle cover gripping elements arranged around a central hub, wherein each gripping element is provided with one or more barbs for gripping the needle cover of said syringe;
provided to said outer cap body, an opposing pair of recessed portions, wherein each said recessed portion defines a recess base, and wherein each recessed portion is bounded by a peripheral lip, the opposing pair of recessed portions being recessed relative to an outer surface of the cap; and
provided to said recess base of each recessed portion, an over-coating,
wherein said cap body comprises a generally rigid material and each said over-coating comprises a more flexible material, and
wherein each said peripheral lip defines a bank that extends beyond the over-coating of the recess base.

2. The cap according to claim 1, wherein the cap body is arranged for mating receipt by a housing of the injector.

3. The cap according to claim 1, wherein the cap body defines a generally rectangular cuboid profile having four generally rectangular cap body sides.

4. The cap according to claim 3, wherein each said recess base with over-coating defines a profile that corresponds with one of the four generally rectangular cap body sides but is recessed relative thereto.

5. The cap according to claim 1, wherein said bank of each peripheral lip rises up in angular fashion from the over-coating of the recess base.

6. The cap according to claim 5, wherein at least forward and rear bank portions of the peripheral lip rise up at an angle of from 30° to 60° from a surface of the over-coating of the recess base.

7. The cap according to claim 1, wherein the over-coating is provided as an over-molding to the recess base.

8. The cap according to claim 1, wherein the cap body comprises a thermoplastic polymer material.

9. The cap according to claim 1, wherein the over-coating comprises a thermoplastic elastomer material.

10. The cap according to claim 9, wherein the thermoplastic elastomer material is selected from styrene-ethylene/butylene-styrene (SEBS) block copolymers, Styrene-Ethylene/Propylene-Styrene (SEPS) block copolymers, Styrene-Butadiene-Styrene (SBS) and thermoplastic vulcanisates (TPV) incorporating vulcanised rubber inclusions.

11. The cap according to claim 1, wherein a protruding pocket is defined at an inner end wall of the inner cap body and the metal connector is arranged for receipt within said protruding pocket.

12. The cap according to claim 11, wherein the plural needle cover gripping elements are arranged to project away from a top inner surface of the inner cap body and towards an open end of the inner cap body.

13. The cap according to claim 1, wherein each said bank does not extend beyond the outer cap body.

14. The cap according to claim 1, wherein said plural needle cover gripping elements project from said central hub of said metal connector.

15. The cap according to claim 1, wherein the outer cap body defines a generally rectangular cuboid profile having four generally rectangular outer cap body sides, and
wherein each said recess base with the over-coating defines an over-coating profile that corresponds with one of the four generally rectangular outer cap body sides but is recessed relative thereto.

16. An injector comprising:
a housing;
a syringe with a needle cover; and
a cap according to claim 1.

17. The injector according to claim 16, further comprising an actuating mechanism,
wherein the syringe comprises a syringe barrel and a plunger, and
wherein the actuating mechanism is configured to provide drive for drivable movement of a drive transfer element for transferring drive to said plunger of the syringe for axial movement thereof within said syringe barrel.

18. The injector according to claim 17, wherein said drive transfer element is a manually operable drive transfer element for transferring axial drive to the plunger of the syringe.

19. The injector according to claim 17, wherein said drive transfer element is an automatically operable drive transfer element for transferring axial drive to the plunger of the syringe; and an energy store for providing drive energy to the drive transfer element.

20. The injector according to claim 16, wherein the cap body defines a generally rectangular cuboid profile having four generally rectangular cap body sides and having a generally square rear opening.

21. The injector according to claim 20, wherein the housing defines a generally square cap-receiving forward profile.

22. The injector according to claim 16, wherein a rear opening of the outer cap body is provided with mating protrusions arranged for mating receipt of a collar provided to a forward end of the housing.

23. The injector according to claim 16, further comprising one or more finger hold elements.

24. The injector according to claim 16, further comprising a handle having a handle body; and an opposing pair of handle arms,
wherein the cap is arranged for receipt by the housing such that the opposing pair of recessed portions on the outer cap body line up with the opposing pair of handle arms.

25. The injector according to claim 16, wherein the syringe contains a liquid drug formulation.

26. The injector according to claim 25, wherein a barrel of said syringe has a volume corresponding to a single dose of said liquid drug formulation.

27. The injector according to claim 26, wherein the liquid drug formulation comprises an aqueous formulation of a therapeutic biologic type drug.

28. A kit, comprising:
an injector comprising:
a housing;
a syringe with a needle cover; and
a cap according to claim 1.

* * * * *